(12) United States Patent
Kielian

(10) Patent No.: US 10,821,178 B2
(45) Date of Patent: Nov. 3, 2020

(54) METHODS OF TREATING BIOFILM INFECTIONS COMPRISING ADMINISTERING INHIBITORS OF MYELOID-DERIVED SUPPRESSOR CELLS

(71) Applicant: BOARD OF REGENTS OF THE UNIVERSITY OF NEBRASKA, Lincoln, NE (US)

(72) Inventor: Tammy Kielian, Omaha, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 136 days.

(21) Appl. No.: 14/908,028

(22) PCT Filed: Jul. 29, 2014

(86) PCT No.: PCT/US2014/048599
§ 371 (c)(1),
(2) Date: Apr. 29, 2016

(87) PCT Pub. No.: WO2015/017402
PCT Pub. Date: Feb. 5, 2015

(65) Prior Publication Data
US 2016/0158353 A1  Jun. 9, 2016

Related U.S. Application Data

(60) Provisional application No. 62/014,864, filed on Jun. 20, 2014, provisional application No. 61/859,500, filed on Jul. 29, 2013.

(51) Int. Cl.
| | | |
|---|---|---|
| *A61K 39/395* | (2006.01) | |
| *A61K 38/18* | (2006.01) | |
| *A61K 38/19* | (2006.01) | |
| *A61K 38/20* | (2006.01) | |
| *A61K 38/21* | (2006.01) | |
| *C12N 5/0786* | (2010.01) | |
| *A61K 45/06* | (2006.01) | |
| *C07K 16/18* | (2006.01) | |
| *C07K 16/28* | (2006.01) | |
| *G01N 33/50* | (2006.01) | |

(52) U.S. Cl.
CPC ...... *A61K 39/3955* (2013.01); *A61K 38/1841* (2013.01); *A61K 38/191* (2013.01); *A61K 38/2066* (2013.01); *A61K 38/217* (2013.01); *A61K 45/06* (2013.01); *C07K 16/18* (2013.01); *C07K 16/28* (2013.01); *C12N 5/0645* (2013.01); *G01N 33/5091* (2013.01); *C12N 2501/231* (2013.01); *G01N 2333/46* (2013.01); *G01N 2800/26* (2013.01)

(58) Field of Classification Search
CPC ............ A61K 39/3955; A61K 38/1841; A61K 38/191; A61K 38/2066; A61K 38/217; A61K 45/06; C07K 16/18; C07K 16/28; C12N 5/0645; G01N 33/5091
See application file for complete search history.

(56) References Cited

U.S. PATENT DOCUMENTS

| | | | | |
|---|---|---|---|---|
| 7,612,045 | B2 * | 11/2009 | Eldridge | A61K 8/63 424/49 |
| 9,803,002 | B2 * | 10/2017 | Brown | C07K 16/1271 |
| 2011/0135739 | A1 | 6/2011 | Carter et al. | |
| 2011/0250300 | A1 | 10/2011 | Biswal et al. | |
| 2011/0256130 | A1 | 10/2011 | Schultz et al. | |
| 2011/0293658 | A1 * | 12/2011 | Cerundolo | A61K 31/00 424/209.1 |
| 2012/0082688 | A1 | 4/2012 | Chen et al. | |
| 2012/0321566 | A1 * | 12/2012 | Liu | C07H 13/08 424/48 |

FOREIGN PATENT DOCUMENTS

| | | | |
|---|---|---|---|
| WO | WO-2012/025186 A1 | 3/2012 | |
| WO | WO-2013/032964 A1 | 3/2013 | |
| WO | WO-2013032964 A1 * | 3/2013 | ............ A61K 38/19 |
| WO | WO-2013/090185 A1 | 6/2013 | |

OTHER PUBLICATIONS

Couper et al., (J Immunol May 1, 2008, 180 (9) 5771-5777).*
Jager et al., (Molecules. Jun. 4, 2009;14(6):2016-31).*
Annapoorani et al., (J Comput Aided Mol Des. Sep. 2012;26(9):1067-77. Epub Sep. 18, 2012).*
Lee et al., (Biochem Pharmacol. May 1, 2007;73(9):1412-21. Epub Dec. 20, 2006; Abstract only).*
Zampini, et al., (Bol Latinoam Caribe Plant Med Aromat. 2013. 12(2): 201—208;epub Mar. 30, 2013).*
Hu et al., (Mol Cancer Ther. Sep. 2008;7(9):2681-91).*
So E.Y., et al. (Oct. 21, 2018) American College of Rheumatology—Meeting Abstracts. Abstract 58.*
Sendo S, et al. (Aug. 6, 2019) Arthritis Res. Ther. 21(1):184. (doi: 10.1186/s13075-019-1963-2).*
So Ey, et al. (Oct. 21, 2018) 2018 ACR/ARHP Annual Meeting. Abstract 58. (https://acrabstracts.org/abstract/inhibition-of-lipid-phosphatase-ship1-expands-myeloid-derived-suppressor-cells-and-attenuates-rheumatoid-arthritis-in-mice/).*
Abu-Amer, Inflammation, cancer, and bone loss, *Curr. Opin. in Pharmacol.*, 9: 427-433 (2009).
Archer et al., Clearance of Staphylococcus aureus nasal carriage is T cell dependent and mediated through interleukin-17A expression and neutrophil influx, *Infect. Immun.*, 81:2070-5.(2013).
Austyn et al., F4/80, a monoclonal antibody directed specifically against the mouse macrophage, *European J. Immunol.*, 11:805-5 (1981).

(Continued)

*Primary Examiner* — Robert S Landsman
(74) *Attorney, Agent, or Firm* — Marshall, Gerstein & Borun LLP

(57) ABSTRACT

Compositions and methods for preventing, ameliorating or treating biofilm infections are provided, including biofilms comprising at least one Pseudomonad or *Staphylococcus*, such as *S. aureus*. The biofilm infections may be associated with artificial joints, prostheses or implants.

7 Claims, 18 Drawing Sheets

(56) References Cited

OTHER PUBLICATIONS

Bernthal et al., A mouse model of post-arthroplasty *Staphylococcus aureus* joint infection to evaluate in vivo the efficacy of antimicrobial implant coatings, *PloS One*, 5:e12580 (2010).
Brudecki et al., Myeloid-derived suppressor cells evolve during sepsis and can enhance or attenuate the systemic inflammatory response, *Infection and immunity*, 80:2026-34 (2012).
Burton et al., 2013. Orthopedic wear debris mediated inflammatory osteolysis is mediated in part by NALP3 inflammasome activation, *J. Orthopaed. Res.: Official publication of the Orthopaedic Research Society*, 31:73-80 (2013).
Carr et al., Specific depletion reveals a novel role for neutrophil-mediated protection in the liver during Listeria monocytogenes infection, *European J. Immunology*, 41:2666-76 (2011).
Cassat et al., A secreted bacterial protease tailors the *Staphylococcus aureus* virulence repertoire to modulate bone remodeling during osteomyelitis, *Cell Host & Microbe*, 13:759-72 (2013).
Cerca et al., *Staphylococcus epidermidis* biofilms with higher proportions of dormant bacteria induce a lower activation of murine macrophages, *J. Med. Microbiol.*, 60:1717-24 (2011).
Chandra et al., Myeloid-derived suppressor cells have a central role in attenuated Listeria monocytogenes-based immunotherapy against metastatic breast cancer in young and old mice, *British J. Can.*, 108:2281-90 (2013).
Cho et al., Neutrophil-derived IL- (beta is sufficient for abscess formation in immunity against *Staphylococcus aureus* in mice, *PLoS pathogens*, 8: e1003047 (2012).
Condamine et al., Molecular mechanisms regulating myeloid-derived suppressor cell differentiation and function, *Trends in Immunol.*, 32: 19-25 (2011).
Cuenca et al., A paradoxical role for myeloid-derived suppressor cells in sepsis and trauma, *Molecular medicine*, 17: 281-92 (2011).
Delano et al., MyD88-dependent expansion of an immature GR-1(+)CD11b(+) population induces T cell suppression and Th2 polarization in sepsis, *J. Exper. Med.*, 204:1463-74 (2007).
Donlan et al., Biofilms: survival mechanisms of clinically relevant microorganisms, *Clinical microbiology reviews*, 15:167-93 (2002).
Epstein et al., Interleukin-1 modulates periprosthetic tissue formation in an intramedullary model of particle-induced inflammation, *J. Orthopaed. Res.: Official publication of the Orthopaedic Research Society*, 23:501-10 (2005).
Eruslanov et al., Pivotal Advance: Tumor-mediated induction of myeloid-derived suppressor cells and M2- polarized macrophages by altering intracellular PGE(2) catabolism in myeloid cells, *J. Leuk. Biol.*, 88:839-48 (2010).
Gabrilovich et al., Myeloid-derived suppressor cells as regulators of the immune system, *Nature Rev. Immunol.*, 9:162-74 (2009).
Gabrilovich et al., The terminology issue for myeloid-derived suppressor cells, *Can. Res.*, 67:425-6 (2007).
Gabrilovich et al.,. Mechanism of immune dysfunction in cancer mediated by immature Gr-1+ myeloid cells, *J. Immunol.*, 166:5398-406 (2001).
Gordon et al., Monocyte and macrophage heterogeneity, *Nature reviews: Immunol.*, 5:953-64 (2005).
Graves et al., Community-associated methicillin-resistant *Staphylococcus aureus* immune evasion and virulence, *J. Molec. Med.*, 88: 109-114 (2010).
Gunther et al., Host defence against *Staphylococcus aureus* biofilms infection: phagocytosis of biofilms by polymorphonuclear neutrophils (PMN), *Molecular immunology*, 46: 1805-1813 (2009).
Hanke et al., Deciphering mechanisms of staphylococcal biofilm evasion of host immunity, *Frontiers in cellular and infection microbiology*, 2:62 (2012).
Hanke et al., MyD88-dependent signaling influences fibrosis and alternative macrophage activation during *Staphylococcus aureus* biofilm infection, *PLoS one*, 7:e42476 (2012).
Hanke et al., Targeting macrophage activation for the prevention and treatment of *Staphylococcus aureus* biofilm infections, *J. Immunol.*, 190:2159-68. (2013).
Haverkamp et al., in vivo suppressive function of myeloid-derived suppressor cells is limited to the inflammatory site, *Eur. J. Immunol.*, 41:749-59 (2011).
Herzenberg et al., Interpreting flow cytometry data: a guide for the perplexed, *Nat. Immunol.*, 7:681-5 (2006).
Ioannou et al., Crucial role of granulocytic myeloid-derived suppressor cells in the regulation of central nervous system autoimmune disease, *J. Immunol.*, 188:1136-46 (2012).
Josefowicz et al., Regulatory T cells: Mechanisms of differentiation and function, *Ann. Rev. Immunol.*, 30:531-64 (2012).
Kristian et al., Biofilm formation induces C3a release and protects *Staphylococcus epidermidis* from IgG and complement deposition and from neutrophil-dependent killing, *J. Infectious dis.*, 197:1028-35 (2008).
Kusmartsev et al., Inhibition of myeloid cell differentiation in cancer: the role of reactive oxygen species, *J. Leukocyte Biol.*, 74:186-96 (2003).
Lee et al., Ly6 family proteins in neutrophil biology, *J. Leukocyte Biol.*, (2013).
Maenhout et al., Enhanced suppressive capacity of tumor-infiltrating myeloid-derived suppressor cells compared to their peripheral counterparts, *International J. Can.*, E134(5):1077-90 (2014).
Makarenkova et al., CD11b+/Gr-1+ myeloid suppressor cells cause T cell dysfunction after traumatic stress, *J. Immunol.*, 176: 2085-94 (2006).
Niska et al., Monitoring bacterial burden, inflammation and bone damage longitudinally using optical and muCT imaging in an orthopaedic implant infection in mice, *PloS one*, 7:e47397 (2012).
Obregon-Henao et al., Gr1(int)CD11b(+) Myeloid-Derived Suppressor Cells in *Mycobacterium tuberculosis* Infection, *PLoS One*, 8:e80669 (2013).
Ochoa et al., Arginase, prostaglandins, and myeloid-derived suppressor cells in renal cell carcinoma, *Clin. Cancer Res.; An Official J. Amer. Assoc. Can. Res.*, 13:721s-6s (2007).
Ollivere et al., Current concepts in osteolysis, *J. Bone and Joint Surg.*, 94: 10-15 (2012).
Ostrand-Rosenberg et al., Myeloid-derived suppressor cells: linking inflammation and cancer, *J. Immunol.*, 182:4499-506 (2009).
Palazzolo-Balance et al., Neutrophil microbicides induce a pathogen survival response in community-associated methicillin-resistant *Staphylococcus aureus*, *J. Immunol.*, 180:500-9 (2008).
Peranzoni et al., Myeloid-derived suppressor cell heterogeneity and subset definition, *Curr. Opin. Immunol.*, 22:238-44 (2010).
Pillay et al., Immune suppression by neutrophils and granulocytic myeloid-derived suppressor cells: similarities and differences, *Cell. Mol. Life Sci.*, 70:3813-27 (2013).
Poe et al., STAT1-regulated lung MDSC-like cells produce IL-10 and efferocytose apoptotic neutrophils with relevance in resolution of bacterial pneumonia, *Muc. Immunol.*, 6:189-9 (2013).
Prabhakara et al., Murine immune response to a chronic *Staphylococcus aureus* biofilm infection, *Infect. Immunit.*, 79:1789-96 (2011).
Prabhakara et al., Suppression of the inflammatory immune response prevents the development of chronic biofilm infection due to methicillin-resistant *Staphylococcus aureus*, *Infect. Immun.*, 79:5010-8 (2011).
Purdue et al., the cellular and molecular biology of periprosthetic osteolysis, *Clin. Orthopaed. Rel. Res.*, 454: 251-61 (2007).
Ribechini et al., Subsets, expansion and activation of myeloid-derived suppressor cells, *Medical Microbiol. Immunol.*, 199:273-81 (2010).
Ribes et al., Resistance of the brain to *Escherichia coli* K1 infection depends on MyD88 signaling and the contribution of neutrophils and monocytes, *Infection and immunity*, 81:1810-9 (2013).
Rieber et al., Flagellin induces myeloid-derived suppressor cells: implications for *Pseudomonas aeruginosa* infection in cystic fibrosis lung disease, *J. Immunol.*, 190:1276-84 (2013).
Rigby et al., Neutrophils in innate host defense against *Staphylococcus aureus* infections, *Seminars in immunopathology*, 34: 237-59 (2012).
Rodriguez et al., L-arginine availability regulates T-lymphocyte cell-cycle progression, *Blood*, 109:1568-73 (2007).

(56) References Cited

OTHER PUBLICATIONS

Rodriguez et al., Arginase I in myeloid suppressor cells is induced by COX-2 in lung carcinoma, *J. Exper. Med.*, 202: 931-9 (2005).
Rodriguez et al., L-arginine consumption by macrophages modulates the expression of CD3 zeta chain in T lymphocytes, *J. Immunol.*, 171:1232-9 (2003).
Saiwai et al., Ly6C+ Ly6G- Myeloid-derived suppressor cells play a critical role in the resolution of acute inflammation and the subsequent tissue repair process after spinal cord injury, *J. Neurochem.*, 125:74-88 (2013).
Sander et al., Hepatic acute-phase proteins control innate immune responses during infection by promoting myeloid-derived suppressor cell function, *J. Exper. Med.*, 207:1453-64 (2010).
Scherr et al., Global transcriptome analysis of *Staphylococcus aureus* biofilms in response to innate immune cells, *Infection and immunity*, 81: 4363-4376 (2013).
Schommer et al., *Staphylococcus epidermidis* uses distinct mechanisms of biofilm formation to interfere with phagocytosis and activation of mouse macrophage-like cells 774A.1, *Infection and immunity*, 79: 2267-76 (2011).
Serafini et al., Myeloid suppressor cells in cancer: recruitment, phenotype, properties, and mechanisms of immune suppression, *Seminars in Can. Biol.*, 16:53-65 (2006).
Serbina et al., Monocyte emigration from bone marrow during bacterial infection requires signals mediated by chemokine receptor CCR2, *Nature immunology*, 7:311-7 (2006).
Shi et al., Interaction of *Staphylococcus aureus* with osteoblasts (Review), *Experimental and therapeutic medicine*, 3:367-370. (2012).
Sica et al., Altered macrophage differentiation and immune dysfunction in tumor development, *J. Clin. Invest.*, 117:1155-66 (2007).
Spiliopoulou et al., Bacterial adhesion, intracellular survival and cytokine induction upon stimulation of mononuclear cells with planktonic or biofilm phase *Staphylococcus epidermidis*, *FEMS microbiology letters*, 330: 56-65 (2012).
Thurlow et al., *Staphylococcus aureus* biofilms prevent macrophage phagocytosis and attenuate inflammation in vivo, *J. Immunol.*, 186: 6585-96 (2011).
Voyich et al., Insights into mechanisms used by *Staphylococcus aureus* to avoid destruction by human neutrophils, *J. Immunol.*, 175: 3907-3919. (2005).
Watkins et al., Current concepts on the virulence mechanisms of meticillin-resistant *Staphylococcus aureus*, *J. Med. Microbial.*, 61:1179-93, (2012).
Wenzel, Health care-associated infections: major issues in the early years of the 21st century. Clinical infectious diseases : An Official Publication of the Infectious Diseases Society of America, 45 Suppl 1:S85-8 (2007).
Wojtasiak et al., Depletion of Gr-1+, but not Ly6G+, immune cells exacerbates virus replication and disease in an intranasal model of herpes simplex virus type 1 infection, J. Gen. Virol., 91:2158-66 (2010).
Xiang et al., Induction of myeloid-derived suppressor cells by tumor exosomes, *J. Internat. du Can.*, 124: 2621-33 (2009).
Zhang et al., Accumulation of myeloid-derived suppressor cells in the lungs during *Pneumocystis pneumonia*, *Infect. Imm.*, 80:3634-41 (2012).
Zhu et al., The Central Role of Arginine Catabolism in T-Cell Dysfunction and Increased Susceptibility to Infection After Physical Injury, *Annals of Surgery*, (2003).
International Search Report and Written Opinion of the International Search Authority, PCT/US2014/48599, dated Jan. 6, 2015.
International Preliminary Report on Patentability, PCT/US2014/48599, dated Feb. 2, 2016.

* cited by examiner

METHODS OF TREATING BIOFILM INFECTIONS COMPRISING ADMINISTERING INHIBITORS OF MYELOID-DERIVED SUPPRESSOR CELLS

CROSS REFERENCE TO RELATED APPLICATIONS

This application claims the priority benefit of provisional U.S. Patent Application No. 61/859,500, filed Jul. 29, 2013, and provisional U.S. Patent Application No. 62/014,864 filed Jun. 20, 2014, each of which is incorporated herein by reference in its entirety.

GOVERNMENT SUPPORT

This invention was made with government support under Grant No. P01 AI083211 awarded by the National Institutes of Health (NIH/NIAID). The government has certain rights in the invention.

FIELD

The disclosed technology generally relates to the field of infectious disease and, more particularly, to materials and methods for preventing, ameliorating or treating biofilm infections.

BACKGROUND

Microorganisms, specifically bacteria, form biofilm, which is an extra-cellular polysaccharide-based organic polymer. These biofilms are heterogeneous bacterial communities encased in a self-produced matrix, i.e., the polysaccharide-based organic polymer, that present a serious health care concern based on their chronicity and recalcitrance to antibiotic therapy (15). Biofilm can also incorporate divalent metal ions that can form a lattice structure consisting of both organic and inorganic mass. Once this formation develops within a system it is very difficult to remove. Biofilm will protect the organisms from antibiotic therapy and allow them to reproduce with the potential to disseminate and establish new sites of infection in the body. The recalcitrance of biofilm infections to a wide range of antibiotic therapies poses a serious threat to human and non-human animal health. Biofilms can form on both natural body surfaces and structures as well as foreign devices, including indwelling catheters and orthopedic implants. The presence of a foreign body increases the likelihood of infection and drastically lowers the threshold for device colonization.

Biofilm infections, also referred to herein as biofilms, represent over 80% of infections, and about 65% of nosocomial infections caused by microorganisms in the developed world involve biofilms. Biofilms also contribute to catheter infections that cause about 10,000 U.S. deaths and more than 11 billion US dollars in losses in hospital costs annually. In addition, 20% of urinary catheters inserted into 5 million U.S. patients have developed biofilm infections. Biofilms are implicated in urinary tract infections that result in medical expenses of 1.6 billion U.S. dollars each year. Worldwide, over 70,000 people have been diagnosed with cystic fibrosis caused by biofilms of *Pseudomonas aeruginosa*. Between 5 to 7 billion U.S. dollars are spent in medical care and productivity losses in the United States due to 25 to 80 million cases annually of biofilm-related food-borne diarrhea and 8,000 to 18,000 cases of biofilm-related Legionnaire's disease. In general, biofilms cost about 500 billion dollars annually, attributable largely to equipment damage, product contamination, energy losses and medical infections.

Biofilm infections have been associated with a variety of diseases and medical conditions beyond cystic fibrosis, including but not limited to, dental caries, periodontitis, infective endocarditis, musculoskeletal infections, necrotizing fasciitis, osteomyelitis, melioidosis, infectious kidney stones, airway infections, otitis media, biliary tract infections, chronic bacterial prostatitis and infections of medical devices (intravenous catheters, artificial joints, contact lenses, cerebrospinal fluid shunts), among others.

Biofilm infections often lead to significant morbidity due to their chronicity and recalcitrance to antibiotics. Bacterial biofilms are associated with catheters, artificial joints (e.g., hip, knee) and other artificial implants, becoming a growing health problem as populations have aged. The frequency of device-related biofilm infections are continuing to rise, with current infection rates totaling 1-2% of primary arthroplasties, 3-5% of all revisions, around 10-50% of short-term urinary catheterizations, and the majority of all patients with long-term catheterization. The incidence of biofilm infections is projected to increase from 17,000 to 266,000 per year by 2030 as the need for arthroplasty in the aging population will exceed 3.8 million surgeries.

These numbers do not take into account the propensity of bacterial biofilms to colonize other medical devices as well as natural body surfaces. Further complicating currently available treatment paradigms is the fact that bacteria within a biofilm are not responsive to conventional antibiotics, which is thought to be the result of altered metabolism and cell growth. Likewise, bacterial biofilms alter host immune responses to favor anti-inflammatory and pro-fibrotic pathways, which also contribute to biofilm persistence. Methicillin-resistant *Staphylococcus aureus* (MRSA) is a common etiologic agent of biofilms and often causes chronic and recurrent infections when associated with indwelling medical devices. The current therapeutic option for managing device-associated biofilm infections is a staged replacement of the hardware, either as a single-step exchange, whereby the entire implant is replaced in a single procedure or, more commonly, as a 2-stage exchange. In the latter case, patients receive extended antibiotic regimens in addition to surgical management, which generally consists of device removal and replacement with an antibiotic-impregnated temporary spacer, followed by insertion of a new prosthesis after a 2- to 8-week period. This is a long and debilitating process associated with significant morbidity and economic impact for patients.

The cycle of prosthesis removal and replacement, which is the current therapeutic option for dealing with biofilm-infected artificial devices, presents an inconvenient, ineffective, and undesirable option. These difficulties in biofilm treatment and control are underscored even further when the biofilm is associated with more permanent artificial implants such as hips, knees, and heart valves. This issue becomes even more pronounced against the backdrop of the rapidly increasing population of the elderly, who will be the primary recipients of such artificial implants and who grow increasingly less immunoresponsive over time.

As noted, conventional antibiotics are ineffective in treating and controlling bacterial burden in biofilms. Nevertheless, they are commonly used to control bacteria that escape the biofilm matrix in order to prevent their colonization of other tissue sites. Such use of antibiotics imposes selection pressures on the bacteria and increases the chance of antibiotic-resistant strains arising. Like surgical intervention, conventional antibiotics do not present an ideal therapeutic option for addressing biofilm infections, including biofilm-fouled implants.

Myeloid-derived suppressor cells (MDSCs) are a heterogeneous population of immature monocytes and granulocytes that are potent inhibitors of T cell activation (1). In mice, MDSCs are characterized by their expression of CD11b and Gr-1, but can be further subdivided into monocyte- and granulocyte-like subsets based on their differential expression of Ly6C and Ly6G, which are referred to as monocyte-like MDSC (M-MDSC) and granulocyte-like MDSC (G-MDSC), respectively (2, 3). CD11b$^+$Gr-1$^+$ cells normally reside in the bone marrow prior to their differentiation into mature granulocytes, macrophages, or dendritic cells. However, MDSCs can be recruited into lymphoid and inflamed tissues during pathologic conditions by the actions of growth factors, such as G-CSF, GM-CSF, and VEGF, where disturbances in cytokine homeostasis block their differentiation into mature myeloid effector cells, resulting in MDSC expansion (3, 4). Several factors influence MDSC activation, including proinflammatory cytokines driven by MyD88-dependent signaling (i.e., IL-6), reactive oxygen species (ROS), and cyclooxygenase-2 (COX-2). These proinflammatory molecules induce the expression of arginase-1 (Arg-1) and several anti-inflammatory cytokines that not only contribute to the inhibition of T cell responses, but may also play a role in macrophage polarization towards an alternatively activated M2 phenotype (4).

Staphylococcus aureus (S. aureus) is a leading cause of community-acquired and nosocomial infections (11, 12). Infection risk is increased by the presence of foreign materials, and S. aureus is a leading cause of biofilm infections on indwelling medical devices and orthopedic implants (13, 14). S. aureus biofilms have been shown to skew macrophages toward an alternatively activated M2 anti-inflammatory phenotype, typified by robust Arg-1 expression that correlates with the failure to recruit T cells to the site of infection (16). Arg-1 expression, however, was also detected in other cell types, leading to an examination of the identity of alternative Arg-1$^+$ cells associated with S. aureus biofilms.

The foregoing discussion highlights the urgent need for new approaches to prevent biofilm formation, maintenance, or growth, and/or to facilitate biofilm eradication, without the need for surgical intervention, or dangerous (ozone) or ineffective (antibiotics) therapeutics. Thus, a need exists in the art for compositions and methods for preventing and treating biofilms that are efficacious and cost-effective without incurring significant risk of toxicity or other complications arising from prophylactic or therapeutic treatment.

SUMMARY

The disclosure provides compositions and methods for the prevention, amelioration, or treatment of biofilm infections. More particularly, the disclosure provides for the targeting of myeloid-derived suppressor cells (MDSCs) to treat biofilm based infection. The disclosed compositions and methods can be used to treat any biofilm infection caused by, or associated with, any known infectious organism, such as microbes including gram-positive and gram-negative bacteria, yeast, and fungi. The biofilm infections may be associated with medical implants or devices such as catheters and joint replacements or natural surfaces found within the body, such as heart valves. Compositions of the disclosure include any compound (synthetic or biologic) that inhibits MDSC function. These compounds include, but are not limited to, antibodies, peptides, small molecules, and/or DNA/RNA based therapeutics. Inhibition of MDSC function includes, but is not limited to, the inhibition of overall function of MDSCs, inhibition of specific functions of MDSCs such as arginase inhibitors, killing of MDSCs, inhibition of MDSC proliferation, and inhibition of formation of new MDSCs. It is further envisioned that the MDSC inhibitors are used in conjunction with other existing drugs such as antibiotics, proteolytic enzymes such as matrix metalloproteinases, MMPs, and collagenase, or activated macrophage therapy, as described in WO 2013/032964.

Disclosed herein are studies identifying a predominant CD11b$^+$Gr-1$^+$Arg-1$^+$ MDSC infiltrate that contributes to the anti-inflammatory environment typical of S. aureus biofilm-associated infections. As disclosed in the following working examples, the functional role of MDSCs in shaping the anti-inflammatory milieu during S. aureus orthopedic biofilm infection was examined. Although MDSCs were identified using well-established markers (17-19), their ability to attenuate T cell proliferation was required to establish their identity as a bona fide MDSC population. It was found that MDSCs infiltrating S. aureus biofilms were capable of inhibiting T cell proliferation, which represents the first report of MDSCs in any type of staphylococcal infection. Furthermore, qRT-PCR analysis of FACS-purified MDSCs revealed increased expression of typical MDSC molecules, including Arg-1, iNOS, and IL-10. Administration of monoclonal antibody 1A8 (anti-Ly6G), which specifically depleted the immunosuppressive MDSC population and mature neutrophils, significantly increased monocyte and macrophage proinflammatory activity, which translated into decreased S. aureus burdens in the infected joint. Consistent with the foregoing discussion, MDSCs were recently identified as the predominant cell type infiltrating S. aureus biofilm infections typified by Arg-1 expression, as disclosed herein.

Evidence to support the importance of monocytes/macrophages in biofilm containment in the absence of MDSCs was obtained by demonstrating that RB6-C85 (anti-Gr-1 or anti-Ly6G/Ly6C) treatment, which depleted effector monocytes and macrophages in addition to MDSCs and granulocytes, significantly increased S. aureus burdens and proinflammatory mediator expression as well as bacterial dissemination to peripheral organs. These results indicate that MDSCs establish an anti-inflammatory milieu during S. aureus biofilm infection that thwarts monocyte and macrophage proinflammatory activity leading to persistent colonization. This prominent MDSC infiltrate also explains the paucity of T cells associated with S. aureus biofilms. Collectively, these studies demonstrate a role for MDSCs during staphylococcal biofilm infection and preventing their immunosuppressive actions provides treatment strategies to mitigate, eliminate or prevent these devastating, chronic infections.

In one aspect, the disclosure provides a method of preventing or treating a biofilm infection comprising administering a therapeutically effective amount of an inhibitor of a myeloid-derived suppressor cell (MDSC). Some embodiments provide for the method wherein the MDSC is a CD11b$^+$Gr-1$^+$ MDSC. In some embodiments, the inhibitor is Gemcitabine, a STAT3 inhibitor, STAT3-targeted siRNA, a Janus kinase (JAK) inhibitor, an anti-CD15 (SSEA-1), an anti-CD33, an anti-CD34, an anti-CD66b, an anti-CD162, an anti-MRP-14 (S100A9), an anti-NF-kB (p50) antibody, an anti-SHIP-1 antibody, an anti-STAT1 antibody, an anti-STAT3 antibody, an indoleamine 2,3-dioxygenase (IDO)

inhibitor, an Nrf-2 activator, an IL-10 inhibitor, an IL-10 receptor inhibitor, or an arginase inhibitor. The disclosure also comprehends the method wherein the arginase inhibitor is C-201 or C-301. In some embodiments of the method, the IDO inhibitor is INCB24360, norharmane, rosmarinic acid, 1-methyltryptophan, a tryptophan derivative, Indoximod, or NLG919. Some embodiments provide for administration of a JAK inhibitor in the form of AZD1480, tofacitinib, ruxolitinib (Jakafi), baricitinib, decernotinib, GPLGO34, CEP-701 (lestaurtinib), INCB39110, INCB16562, INCB47986, SB1518 (pacritinib), SAR302503, XL019, or NVP-BSK805. In some embodiments, the STAT3 inhibitor is stattic, galiellalactone, a galiellalactone analog, GLG-101, GLG-202, GLG-302, GLG-401, or OPB-31121. In some embodiments, the Nrf-2 activator is RTA-408.

In addition, embodiments are contemplated wherein the biofilm is associated with an artificial substance in vivo, such as wherein the artificial substance is an implant or a prosthesis. In some embodiments, the biofilm infection is a *Staphylococcus* infection or a *Pseudomonas* infection. Exemplary *Staphylococcus* infections are caused by *Staphylococcus aureus* such as methicillin-resistant *S. aureus* (MRSA). Exemplary *Pseudomonas* infections are caused by *Pseudomonas aeruginosa*.

Another aspect of the disclosure provides a method of preventing or treating inflammatory activity in a subject with a biofilm infection comprising administering a therapeutically effective amount of an inhibitor of a MDSC. In some embodiments, the inhibitor is Gemcitabine, a STAT3 inhibitor, STAT3-targeted siRNA, a Janus kinase (JAK) inhibitor, an anti-CD15 (SSEA-1) antibody, an anti-CD33 antibody, an anti-CD34 antibody, an anti-CD66b antibody, an anti-CD162 antibody, an anti-MRP-14 (S100A9) antibody, an anti-NF-kB (p50) antibody, an anti-SHIP-1 antibody, an anti-STAT1 antibody, an anti-STAT3 antibody, an indoleamine 2,3-dioxygenase (IDO) inhibitor, an Nrf-2 activator, an IL-10 inhibitor, an IL-10 receptor inhibitor, or an arginase inhibitor. In some embodiment, the arginase inhibitor is C-201 or C-301. In some embodiments, the IDO inhibitor is INCB24360, norharmane, rosmarinic acid, 1-methyltryptophan, a tryptophan derivative, Indoximod, or NLG919. Some embodiments are provided wherein the JAK inhibitor is AZD1480, tofacitinib, ruxolitinib (Jakafi), baricitinib, decernotinib, GPLGO34, CEP-701 (lestaurtinib), INCB39110, INCB16562, INCB47986, SB1518 (pacritinib), SAR302503, XL019, or NVP-BSK805. The disclosure also comprehends embodiments wherein the STAT3 inhibitor is stattic, galiellalactone, a galiellalactone analog, GLG-101, GLG-202, GLG-302, GLG-401, or OPB-31121. Some embodiments provide for administration of a NR-2 activator wherein the Nrf-2 activator is RTA-408. Some embodiments provide the method wherein the MDSC is a CD11b⁺Gr-1⁺ MDSC. In some embodiments, the disclosure provides a method wherein the biofilm is associated with an artificial substance in vivo, such as wherein the artificial substance is an implant or a prosthesis. As with other aspects of the disclosure, embodiments are contemplated wherein the biofilm infection is a *Staphylococcus* infection or a *Pseudomonas* infection. Exemplary *Staphylococcus* infections are *Staphylococcus aureus* infections, such as methicillin-resistant *S. aureus* (MRSA). Exemplary *Pseudomonas* infections are *Pseudomonas aeruginosa* infections.

Yet another aspect of the disclosure is a method of preventing or treating a biofilm infection comprising administering a therapeutically effective amount of a pro-inflammatory stimulator of a monocyte or macrophage. This could include the administration of M1-activated macrophages, as described in WO 2013/032964, incorporated herein by reference, or administration of exogenous cytokines such as IFN-γ, TNF-α, or neutralization of anti-inflammatory molecules that can be secreted by MDSCs to inhibit anti-biofilm responses, including IL-10 or TGF-β. More particularly, the disclosure comprehends a method of preventing or treating a biofilm infection comprising administering a therapeutically effective amount of a stimulator of a monocyte. In some embodiments, the stimulator of a monocyte is IFN-γ or TNF-α. Some embodiments further comprise administration of an M1-activated macrophage. In some embodiments, the method further comprises administration of an inhibitor of an anti-inflammatory molecule secreted by a MDSC selected from the group consisting of IL-10 and TGF-β. In some embodiments, the monocyte is an effector Ly-6C monocyte.

Still another aspect of the disclosure is a method of inhibiting the accumulation of a bacterial biofilm infection of an implant, a prosthesis, or a natural or artificial joint, comprising administering a therapeutically effective amount of an inhibitor of a MDSC.

A related aspect of the disclosure provides a method of reducing the number of MDSCs comprising administering a therapeutically effective amount of an inhibitor of IL-10 or the IL-10 receptor. In some embodiments, the inhibitor of IL-10 is an anti-IL-10 antibody, an anti-IL-10 receptor antibody, including any antibody form of the foregoing antibodies that is known in the art (e.g., single-chain antibody, scFv, fusion), Rituximab, Sorafenib, AS101, or a bispecific anti-CD11b anti-GR-1 antibody.

Yet another aspect of the disclosure is a method of diagnosing a biofilm infection comprising: (a) obtaining a sample from a subject; (b) measuring a myeloid-derived suppressor cell (MDSC) infiltrate or MDSC activation status; and (c) diagnosing a biofilm infection based on the level of MDSC infiltrate or MDSC activation. The measuring of MDSC infiltrates involves quantitating MDSC infiltrates in some embodiments.

Other features and advantages of the disclosure will become apparent from the following detailed description, including the drawing. It should be understood, however, that the detailed description and the specific examples, while indicating preferred embodiments, are provided for illustration only, because various changes and modifications within the spirit and scope of the disclosure will become apparent to those skilled in the art from the detailed description.

DETAILED DESCRIPTION

Figure 1:
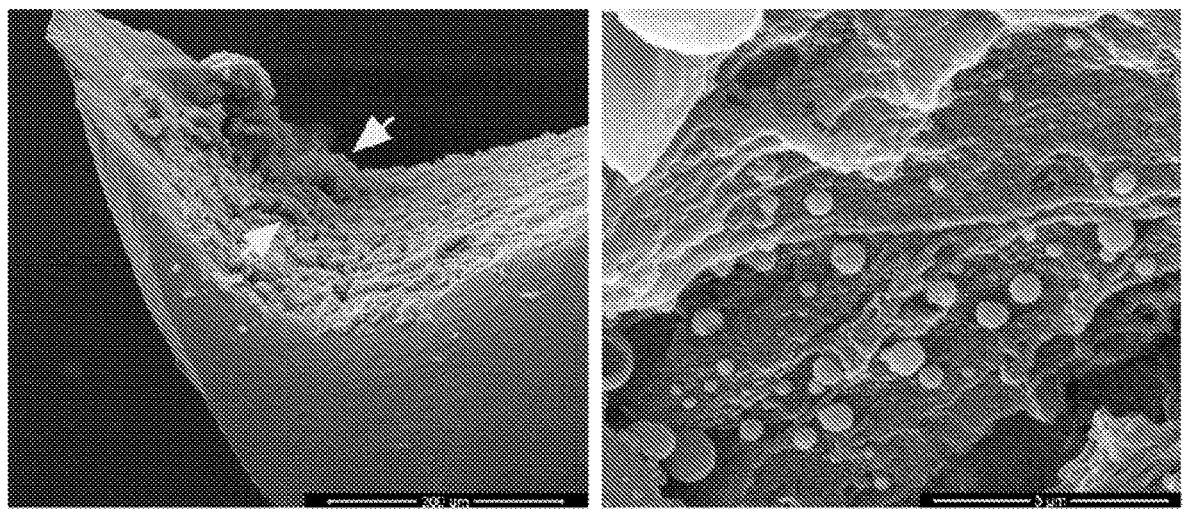
FIG. 1. Demonstration of *S. aureus* biofilm formation in vivo on orthopedic implants. Titanium orthopedic implants were isolated from wild type mice at day 28 following *S. aureus* infection and processed for SEM analysis. (A) Biofilm formation is visible on the concave surface of the implant (300× magnification) demonstrating the irregular pattern of the biofilm surface with tower structures visible (arrows); (B) Higher magnification of the biofilm surface revealing numerous cocci interspersed with matrix material (20,000× magnification). The image has been pseudocolored to highlight *S. aureus* (gold).

The disclosure provides compositions and methods for preventing, ameliorating or treating biofilm infections by reducing or eliminating the effect of myeloid-derived suppressor cells (MDSCs) on the establishment and/or maintenance of biofilm infections. The compositions and methods disclosed herein are suitable for preventing, ameliorating or treating biofilm infections comprising any bacterium, a member of the Fungi Kingdom (e.g., yeast, fungus), or single-celled protozoan, and are suitable for biofilms found in any vertebrate (e.g., mammal, including man), regardless of whether the biofilm is found associated with a natural structure (e.g., a joint) or an artificial structure (e.g., a catheter, a prosthesis, a replacement joint or bone, or an implant).

Studies disclosed herein demonstrate that MDSCs represent the major leukocyte infiltrate associated with two distinct models of S. aureus biofilm infection (i.e., orthopedic device and catheter). Confirmation of the immune suppressive properties of these cells has been demonstrated by the ability of MDSCs recovered from the site of S. aureus orthopedic infection to inhibit T cell proliferation, which is a hallmark of MDSC action, as well as by showing the ability of these MDSCs to actively inhibit the influx of professional phagocytes (i.e., monocytes/macrophages) into sites of biofilm infection. Depletion of MDSCs using antibody-mediated strategies results in a significant reduction in biofilm burdens, likely because the inhibitory action of MDSCs has been negated, allowing anti-microbial effector responses (primarily mediated via macrophage activation) to proceed. It is also expected that the compositions and methods disclosed herein are suitable for use in combination with activated macrophage therapy, as disclosed in WO 2013/032964, incorporate herein by reference.

This disclosure provides compositions and methods to conveniently and effectively treat biofilm infections (e.g., bacterial biofilm infections) associated with catheters and other artificial implants.

The data disclosed herein demonstrate that depleting MDSCs, such as by antibody-mediated approaches, significantly facilitates the clearance of biofilm-associated bacteria from infected medical devices as well as from the surrounding tissue. Given the growing prevalence of nosocomial infections and biofilm development, the increased use of procedures that can give rise to biofilm development, the growing elderly population who will be receiving artificial implants, and the difficulties of treating/controlling bacteria within a biofilm, it is important to develop new approaches to the prevention, amelioration and treatment of biofilm infection, such as by targeting immunosuppressive populations that accumulate at the infection site, such as MDSCs, in both the young and the elderly.

There are several strategies suitable for eliminating MDSCs in the field of cancer biology, including the use of Gemcitabine. In addition to these approaches, an antibody-mediated strategy is disclosed in the working examples described herein, which represents another viable technology for manipulating MDSCs to facilitate biofilm clearance. Reducing MDSC influx into biofilm infections not only appears to be effective in treating bacterial burdens associated with biofilms, this strategy has the added advantage of doing so by targeting the host's own innate immune cells, thus eliminating or minimizing selection pressures imposed directly on the bacteria by antibiotics, decreasing the likelihood of resistant strains.

MDSCs are a heterogeneous population of immature monocytes and granulocytes that are potent inhibitors of T cell activation. A role for MDSCs in bacterial infections has only recently emerged. Because $S.$ $aureus$ biofilms are capable of subverting immune-mediated clearance, MDSCs were examined to determine if they could play a role in this process. CD11b$^+$Gr-1$^+$ MDSCs represented the main cellular infiltrate during $S.$ $aureus$ orthopedic biofilm infection, accounting for over 75% of the CD45$^+$ population. Biofilm-associated MDSCs inhibited T cell proliferation and cytokine production, which correlated with a paucity of T cell infiltrates at the infection site. Analysis of FACS-purified MDSCs recovered from $S.$ $aureus$ biofilms revealed increased Arg-1, iNOS, and IL-10 expression, key mediators of MDSC suppressive activity. Targeted depletion of MDSCs and neutrophils using the monoclonal antibody (mAb) 1A8 (anti-Ly6G) improved bacterial clearance by enhancing the intrinsic pro-inflammatory attributes of infiltrating monocytes and macrophages. Furthermore, the ability of monocytes/macrophages to promote biofilm clearance in the absence of MDSC action was revealed with RB6-C85 (anti-Gr-1 or anti-Ly6G/Ly6C) administration, which resulted in significantly increased $S.$ $aureus$ burdens both locally and in the periphery, since effector Ly-6C monocytes and by extension, mature macrophages, were also depleted. Collectively, these results are the first to demonstrate that MDSCs are key contributors to the chronicity of $S.$ $aureus$ biofilm infection, as their immunosuppressive function prevents monocyte/macrophage proinflammatory activity, which facilitates biofilm persistence.

An emerging role for MDSCs has been described in several diseases aside from cancer, most recently to include bacterial infections (7-10, 42, 47). Using a mouse model of $S.$ $aureus$ orthopedic biofilm infection, a population of CD11b$^+$Gr-1$^+$ MDSCs was shown to accumulate in the joint tissue, and depletion of this population resulted in improved bacterial clearance by promoting the proinflammatory attributes of infiltrating monocytes and macrophages. This is the first disclosure of a functional role for MDSCs in any type of staphylococcal or biofilm infection and indicates that MDSCs are key contributors to the chronicity of $S.$ $aureus$ biofilms through their modulation of the host immune response.

It has been shown that $S.$ $aureus$ biofilms augment Arg-1 expression and polarize macrophages toward an M2 anti-inflammatory state (16). The current study has expanded the repertoire of immune suppressive effectors to include MDSCs. MDSCs are notable for their robust Arg-1 expression, which depletes extracellular arginine, causing T cell dysfunction at multiple levels, including cell cycle arrest, reduced expression of the CD3ζ chain, and a global reduction in several proteins essential for T cell activity (48-51). Limited numbers of CD4$^+$ T cells were detected in implant-associated tissues during $S.$ $aureus$ biofilm infection (i.e., 2-5%). It was expected that T cell infiltrates would be enhanced following Gr-1 and Ly6G depletion originating from the loss of MDSC activity; however, this was not the case. One possibility to explain this finding is that the combined action of MDSCs and regulatory cytokines serve to limit T cell numbers at the site of biofilm infection. Besides actions on T cells, arginine depletion via MDSC Arg-1 activity reduces its availability for iNOS, which thwarts M1 classical macrophage activation, as has been shown in $S.$ $aureus$ biofilms (16).

By extension, the significant MDSC infiltrate associated with $S.$ $aureus$ biofilms in vivo is likely an important factor in skewing monocytes/macrophages towards a M2 anti-inflammatory phenotype that promotes bacterial persistence. The studies disclosed herein confirmed that MDSCs recovered from the site of orthopedic biofilm infection express Arg-1 and IL-10. Depletion of the suppressive MDSC population was thus expected to allow infiltrating monocytes to act as true effector cells. This was confirmed by the finding that Ly6C$^+$ monocytes recovered from MDSC depleted animals expressed a wide array of proinflammatory genes compared to monocytes recovered from IgG treated mice where the MDSC population remained intact. In addition, MDSC depletion significantly decreased biofilm burdens, confirming the importance of this population in orchestrating the anti-inflammatory biofilm milieu to facilitate infection persistence. Besides MDSCs, regulatory T cells (Tregs) also possess anti-inflammatory attributes similar to MDSCs (52). However, no CD4$^+$CD25$^+$Foxp3$^+$ cells associated with $S.$ $aureus$ biofilm infections were detected, whereas another group has reported Treg involvement in biofilm clearance (33). Based on the analysis disclosed herein, it is expected that MDSCs represent the main immunosuppressive effector cell during $S.$ $aureus$ orthopedic biofilm infection.

Figure 17:
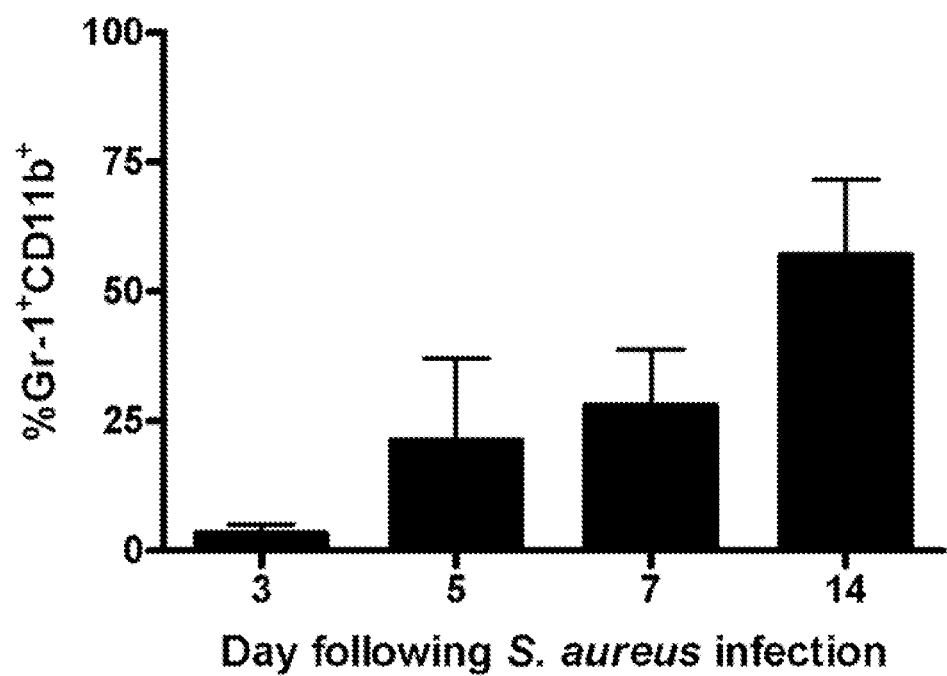
FIG. 17. $CD11b^+Gr-1^+$ MDSC infiltrates are observed during S. aureus catheter-associated biofilm infection. Mice (n=4 per time point) were infected with $10^3$ CFU of USA300 LAC::lux in the lumen of surgically implanted catheters to establish biofilm infection. Catheter-associated tissues were collected from mice at the indicated time points, whereupon $CD11b^+Gr-1^+$ infiltrates were quantitated by flow cytometry. Results are presented as the percentage of the total $CD45^+$ infiltrate.
Figure 18:
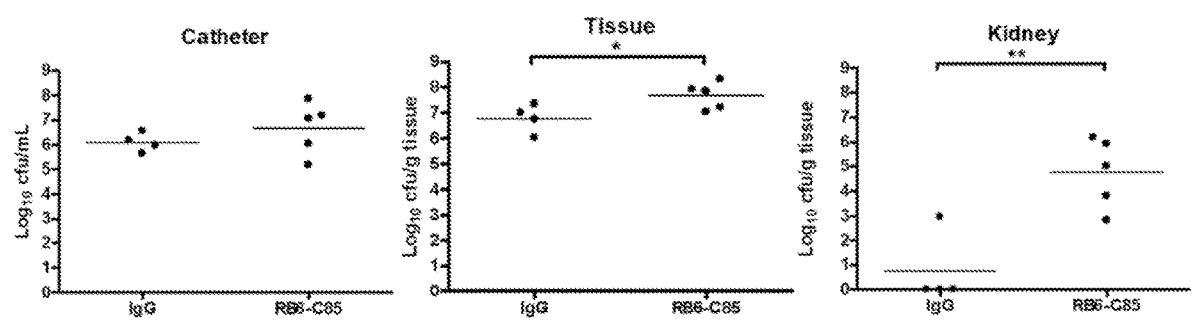
FIG. 18. RB6-C85 treatment during S. aureus catheter-associated biofilm infection results in increased bacterial burdens and dissemination. Mice (n=4 IgG and 5 RB6-C85 per time point) were infected with $10^3$ CFU of USA300 LAC::lux in the lumen of surgically implanted catheters to establish biofilm infection. Animals received i.v. injections of 100 µg RB6-C85 or IgG isotype control antibody at days—1, 2, and 5 following S. aureus exposure, whereupon bacterial burdens associated with infected catheters, surrounding tissue, and dissemination to the kidney were quantitated at day 7 post-infection. Significant differences between groups are denoted by asterisks (*, $p<0.05$; **, $p<0.01$; unpaired two-tailed Student t-test).

RB6-C85 depletion studies revealed significant increases in bacterial dissemination from the orthopedic infection site. As mentioned previously, RB6-C85 recognizes both Ly6G and Ly6C epitopes, effectively depleting MDSCs, neutrophils, monocytes, and by extension, macrophages. Therefore, although MDSC infiltrates were reduced, effector populations were also targeted, leaving fewer leukocytes either locally or systemically to prevent $S.$ $aureus$ dissemination to peripheral organs. By extension, the function of each leukocyte subset is expected to differ depending on the local microenvironment; namely, although the inhibitory actions of MDSCs were negated following RB6-C85 treatment, this coincided with a local reduction in inflammatory monocytes/macrophages, such that biofilm growth could not be held in check at the primary infection site (i.e., joint). When biofilm-associated bacteria seeded peripheral sites, the paucity of systemic neutrophils likely accounted for the failure to effectively clear the infection, which is essential since neutrophils are a main effector cell against planktonic $S.$ $aureus$ (53-56). Dissemination was not observed with anti-Ly6G antibody treatment, which was attributed to the local monocyte/macrophage population that remained intact and exhibited heightened proinflammatory activity. MDSC infiltrates were also detected in a $S.$ $aureus$ catheter-associated biofilm infection model (FIG. 17) and RB6-C85 treatment similarly increased bacterial burdens and dissemination (FIG. 18), providing independent confirmation that MDSCs are a hallmark of $S.$ $aureus$ biofilm infection.

One notable finding in the studies disclosed herein was the extensive extramedullary hematopoiesis observed in the spleens of RB6-C85-treated animals compared to isotype controls. Extramedullary hematopoiesis is frequently seen during chronic inflammatory diseases and cancer (19), and expansion of CD11b$^+$Gr-1$^+$ MDSCs has been reported in tumor and polymicrobial sepsis models (7, 57, 58). During infection, the requirement for myeloid cells dramatically increases in response to an expanding infectious burden, which creates a need for emergency myelopoiesis and the mobilization of immature myeloid cells from the bone marrow and spleen (19). The targeted reduction in Gr-1$^+$ cells coincident with increasing biofilm burdens with RB6-C85 treatment likely explains the extensive extramedullary hematopoiesis observed in the spleens of these animals. Another unexpected finding was that Gr-1$^+$ (Ly6G/Ly6C) infiltrates were increased at the site of orthopedic infection following RB6-C85 administration. However, this was likely a compensatory mechanism in response to elevated bacterial burdens both locally and systemically in Gr-1-depleted mice, since these newly recruited Ly6G$^+$Ly6C$^+$ cells were unable to suppress CD4$^+$ T cell proliferation, which agrees with reports of polymicrobial sepsis (7). In addition, enhanced levels of G-CSF, IL-6, and VEGF were also observed in the serum of RB6-C85-treated mice, all of which contribute to the expansion of immature myeloid cell populations (2, 4). Alternatively, the failure to deplete Ly6G$^+$Ly6C$^+$ infiltrates at later intervals could be explained by the induction of anti-rat IgG antibodies that would be expected to impair the efficacy of RB6-C85 treatment (rat anti-mouse Gr-1). However, this appears less likely because RB6-C85 was still capable of significantly reducing inflammatory monocyte and macrophage infiltrates into *S. aureus* infected joints two weeks after repeated antibody administration.

Live CT scans revealed significantly more osteolysis in the femurs of RB6-C85-treated animals compared to 1A8 and isotype control mice, which may be attributed to the increased bacterial burdens in the former. The exact mechanisms of osteolysis are still not completely understood, and differ depending on pathologic conditions (59, 60). However, several studies suggest that proinflammatory mediators, such as IL-1β, could play a role in the initiation and progression of osteolysis (61-63) and numerous proinflammatory mediators were significantly elevated in the joint and surrounding soft tissue following RB6-C85 treatment, including IL-1β that coincided with increased bone destruction. Additionally, *S. aureus* is not only capable of colonizing the bone matrix, it can also invade osteoblasts, which could contribute to chronicity (64). Furthermore, *S. aureus* internalization by osteoblasts can lead to apoptosis and disrupt the balance of osteoblast and osteoclast activities, which could facilitate bone destruction.

The studies disclosed herein explore the role of MDSCs during *S. aureus* infection. By manipulating these cells with antibody depletion strategies, it was demonstrated that their immunosuppressive function prevents monocytes/macrophages from eliminating biofilm-associated bacteria by attenuating their proinflammatory properties. These findings do not exclude the possibility that the biofilm matrix may also play a role in thwarting immune recognition in vivo; however, this remains an area of debate. Although it is clear that intact biofilms do afford some degree of protection against macrophage phagocytosis (16, 23, 66-69), it is clear that neutrophils are fully capable of invading and phagocytosing biofilm-associated bacteria (23, 70-72), yet there is no apparent impact on biofilm growth. The fact that staphylococcal biofilms polarize macrophages towards an alternatively activated M2 phenotype does indicate that macrophage surface receptors are triggered to elicit this programming event. Preventing the immunosuppressive action of infiltrating MDSCs offer a new therapeutic strategy to thwart these devastating, chronic infections.

Example 1

Materials and Methods

Mice.

Male C57BL/6 mice (8 weeks of age) were purchased from the National Cancer Institute (Frederick, Md.). These studies were performed in strict accordance with recommendations found in the Guide for the Care and Use of Laboratory Animals of the National Institutes of Health. The animal use protocol was reviewed by the Institutional Animal Care and Use Committee of the University of Nebraska Medical Center.

Mouse Model of *S. aureus* Orthopedic Biofilm Infection.

To simulate infectious complications in patients following surgical device placement, a mouse *S. aureus* orthopedic implant infection model was utilized as previously described with minor modifications (20). Animals were anesthetized with ketamine/xylazine (Hospira, Inc., Lake Forest, Ill. and Akorn, Inc., Decatur, Ill.; 100 mg/kg and 5 mg/kg, respectively) and the surgical site was disinfected with povidone-iodine. A medial parapatellar arthrotomy with lateral displacement of the quadriceps-patella was performed to access the distal femur. A burr hole was created in the femoral intercondylar notch extending into the intramedullary canal using a 26-gauge needle, whereupon a pre-cut 0.8 cm orthopedic-grade Kirschner (K)-wire (0.6 mm diameter, Nitinol [nickel-titanium]; Custom Wire Technologies, Inc., Port Washington, Wis.) was inserted into the intramedullary canal, leaving approximately 1 mm protruding into the joint space. A total of $10^3$ colony forming units (CFU) of the bioluminescent *S. aureus* USA300 LAC::lux isolate (16) was inoculated at the implant tip. In some experiments, control mice received sterile implants using an identical procedure. Animals received Buprenex (0.1 mg/kg s.c.; Reckitt Benckiser, Hull, England) immediately after infection and 24 hours later for pain relief. After this interval, all mice exhibited normal ambulation and no discernable pain behaviors.

Scanning Electron Microscopy (SEM).

Mice were sacrificed at day 28 following *S. aureus* infection, whereupon the whole femur harboring the titanium implant was fixed in 0.1 M Sorensen's phosphate buffer containing 2% glutaraldehyde and 2% paraformaldehyde for 1 hour at room temperature and held in fixative overnight at 4° C. Fixed specimens were washed three times in Tris-buffered saline followed by three rinses in ddH$_2$O and decalcification in 14% EDTA for two days. After rinsing in ddH$_2$O, each specimen was dehydrated using a graded series of ethanol washes and the critical point dried in a Pelco CPD2 critical point dryer (Ted Pella, Inc., Redding, Calif.). Dried specimens were mounted on aluminum stubs with carbon tabs and colloidal silver paste and sputter-coated with gold-palladium using a Hummer VI sputter coater (Anatech, LTD, Battle Creek, Mich.). Samples were viewed using a Quanta 200 scanning electron microscope (FEI, Hillsboro, Oreg.) operated at 25 Kv.

In Vivo Depletion Studies.

To deplete MDSCs in vivo, mice received i.p. injections of either 1A8 (anti-Ly6G) or RB6-C85 (anti-Gr-1) antibodies (100 μg/each) one day prior to *S. aureus* infection and every 72 hours thereafter until sacrifice. Control mice received equivalent amounts of isotype-matched control antibodies (rat IgG2a and IgG2b, respectively) using the same treatment regimen. All antibodies were purchased in Ultra-LEAF form (low endotoxin, azide-free) from BioLegend (San Diego, Calif.). Animals were euthanized at 7 or 14 days after infection to determine the impact of cell depletion on *S. aureus* persistence and tissue-associated leukocyte infiltrates. Bone marrow and splenocytes were also collected to determine the efficiency of Antibody-mediated depletion. A separate model of *S. aureus* catheter-associated biofilm infection was utilized in some experiments, as previously described, to confirm the action of RB6-C85 antibody depletion (16, 21).

Computed tomography (CT) of *S. aureus* orthopedic biofilm infections.

Bone integrity in the context of Gr-1$^+$ cell depletion during *S. aureus* orthopedic biofilm infection was monitored using live CT scans. Briefly, mice were anesthetized with 1.5% isoflurane in a 70% nitrous oxide/30% oxygen mixture and imaged using a FLEX Triumph X-ray computed tomography/single photon emission computed tomography (CT/SPECT) system and software (TriFoil Imaging, Inc., Northridge, Calif.). 1024 CT projections for each image were acquired at 75 kVp and reconstructed using Triumph X-O 4.1. CT images were generated using the 3D image visualization and analysis software VIVID, which is based on Amira 4.1 (TriFoil Imaging, Inc.).

Recovery of Orthopedic Implant and Surrounding Tissues for *S. aureus* Enumeration.

For collecting inflamed soft tissue surrounding the infected knee joint, the skin was removed and the subcutaneous tissue dorsal to the patellar tendon was excised, weighed, and processed for flow cytometry as described below. Muscle and tendon tissues were excluded from the analysis. After processing, a small aliquot was removed for quantitation of bacterial burdens. Next, the implant was extracted from the femur and sonicated for 5 minutes in 1 ml of PBS to dislodge bacteria from the implant. The knee joint (including cartilage and ligaments) and femur were homogenized using two sequential procedures due to the resilient nature of these tissues. Initially a 30-second dispersal was performed using a hand-held homogenizer, followed by disruption in a Bullet Blender (Next Advance, Inc., Averill Park, N.Y.) using 100 μm stainless steel beads (0.9-2.0 mm stainless steel blend). After centrifugation, serial 10-fold dilutions of tissue, knee, or femur homogenates as well as implant sonicates were plated on trypticase soy agar with 5% sheep blood (Remel Products, Lenexa, Kans.). Titers were expressed as CFU per gram of tissue or per ml of sonicate fluid for titanium implants. Remaining homogenates were centrifuged (20,000×g, 20 minutes) and frozen at −80° C. for further analysis by MILLIPLEX bead arrays, as described below.

Morphologic and Histologic Analyses.

To confirm that FACS-purified CD11b$^+$Gr-1$^+$ and Ly6G$^+$Ly6C$^+$ cells recovered from infection sites appeared morphologically similar to MDSCs, cells were adhered to glass slides by cyto-centrifugation (Cytopro, Wescor; Logan, Utah) and stained with StainRITE (Polysciences, Inc., Warrington, Pa.). Images were obtained using a Zeiss Axioskop 40 microscope (Zeiss, Thornwood, N.Y.). For hematoxylin and eosin (H&E) staining, implant-associated tissues were fixed in 10% formalin and washed with ddH$_2$O prior to decalcification (Super Decalcification I-Delicate Decalcifier, Polysciences, Inc., Warrington, Pa.), according to the manufacturer's instructions. Decalcified tissue was washed thoroughly with ddH$_2$O before an incision was made in the quadriceps muscle and the femur to remove the implant. Tissues were then embedded in paraffin, with 4 μm sections mounted for H&E staining. H&E-stained tissues were evaluated for inflammatory changes by a board-certified pathologist (J.A.K.) with the degree of inflammation determined using a scoring scale ((0), no observable pathology; (1), low; (2), moderate; and (3), severe pathology). To evaluate splenic architecture following antibody-mediated cell depletion, spleens were fixed in 10% formalin, paraffin embedded, and sectioned for H&E staining.

MILLIPLEX Multi-Analyte Bead Array.

To evaluate the effects of Ly6G- versus Gr-1-mediated cell depletion on the inflammatory milieu during *S. aureus* orthopedic biofilm infection, a custom-designed mouse microbead array was used (MILLIPLEX; Millipore Corporation, Billerica, Mass.), which detects the following mediators: G-CSF, GM-CSF, IFN-γ, IL-1α, IL-1β, IL-2, IL-4, IL-5, IL-6, IL-7, IL-9, IL-10, IL-12p70, IL-13, IL-15, IL-17, CCL2, CCL3, CCL5, CXCL1, CXCL2, CXCL9, CXCL10, TNF-α and VEGF. A Bio-Plex workstation (Bio-Rad, Hercules, Calif.) was used to analyze results and values were normalized to the total amount of protein recovered from each sample.

Flow Cytometry.

To characterize leukocyte infiltrates in inflamed soft tissues surrounding the knee joint during *S. aureus* biofilm infection, tissues were excised, dissociated using the rubber end of a plunger from a 3 cc syringe, and passed through a 35 inn filter (BD Falcon, Bedford, Mass.). The resulting filtrate was washed with 1×PBS and cells were collected by centrifugation (300×g, 10 minutes), whereupon red blood cells (RBCs) were lysed using BD Pharm Lyse (BD Biosciences; San Diego, Calif.). After lysis, cells were resuspended in PBS containing 2% FBS, followed by incubation in Fc Block (BD Biosciences, San Diego, Calif.) to minimize non-specific antibody binding. Cells were stained with CD45-APC, Ly6G-PE, Ly6C-PerCPCy5.5, F4/80-PE Cy7, CCR2-FITC (R&D Systems; Minneapolis, Minn.), and CD11b-eFluor450. All fluorochrome-conjugated antibodies were purchased from BD Biosciences (San Diego, Calif.) or eBioscience (San Diego, Calif.), unless otherwise indicated. An aliquot of cells was stained with isotype-matched control antibodies to assess the degree of non-specific staining and fluorescence minus one was used to identify gating thresholds (22). The number of events analyzed ranged from 20,000-100,000 per sample, depending on the experimental setup. Analysis was performed using BD FACSDiva software with cells gated on the total leukocyte population (CD45$^+$).

MDSC Recovery from *S. aureus* Orthopedic Biofilm Infections for T Cell Proliferation Assays.

MDSCs were collected from the soft tissues surrounding infected knee joints as described above, using either Gr-1-PE and CD11b-FITC or Ly6G-PE, Ly6C-PerCP Cy5.5 and CD11b-eFluor450 depending on the experimental setup. For comparisons, CD11b$^+$Gr-1$^+$ MDSCs were isolated from the spleens of naïve and *S. aureus*-infected animals. The purity of MDSC populations was not examined post-sort due to limiting cell numbers. However, cytospins and gene expression analysis revealed that sorted MDSCs were highly enriched, as they displayed characteristic markers and nuclear morphologies consistent with that reported for MDSCs in the literature. For CD4$^+$ T cell isolation, spleens from naïve mice were pressed through a 250 μm Nitex filter (Genesee, San Diego, Calif.) to generate a single-cell suspension. RBCs were lysed using BD Pharm Lyse and splenocytes were incubated in Fc Block and subsequently stained with CD4-Pacific blue (BD Biosciences). CD4$^+$ T cells collected by FACS were greater than 95% pure and were immediately labeled with efluor670 Cell Proliferation Dye (eBioscience) according to the manufacturer's instructions.

For establishing the functional activity of MDSCs associated with *S. aureus* orthopedic biofilm infections, T cell proliferation assays were performed. Briefly, efluor670-labeled CD4$^+$ T cells were plated at 1.5×10$^5$ cells/well in a 96-well round bottom plate in RPMI-1640 with 10% FBS, supplemented with 100 ng/ml recombinant mouse IL-2 (Invitrogen; Frederick, Md.). FACS-purified Gr-1$^+$CD11b$^+$ (MDSCs), Ly6G$^{high}$Ly6C$^+$ (MDSCs), Ly6G$^{low}$Ly6C$^{low}$ (neutrophils), or Ly6G$^-$Ly6C$^+$ (monocytes) cells were added at 1:1 or 1:5 ratios to CD4$^+$ T cells subjected to polyclonal stimulation with CD3/CD28 Dynabeads (Gibco; Oslo, Norway), because TCR immunodominant epitopes for S. aureus are not defined. Cells were incubated at 37° C. for 72 hours, whereupon the extent of T cell proliferation was determined by flow cytometry and supernatants were saved for cytokine evaluation by MILLIPLEX analysis.

Quantitative Real-Time Reverse Transcription-PCR (qRT-PCR).

Ly6G$^{high}$Ly6C$^+$ MDSCs and Ly6G$^-$Ly6C$^+$ inflammatory monocytes from S. aureus infected tissues were purified by FACS, whereupon total RNA was immediately isolated using the TaqMan Gene Expression Cells-to-CT™ Kit (Ambion, Austin, Tex.). qRT-PCR was performed using TaqMan primer/probe mixes (Foster City, Calif.) for the following genes of interest: iNOS, Arg-1, COX-2, IL-10, IL-13, and IL-12p40. Gene expression levels were normalized to glyceraldehyde 3-phosphate dehydrogenase (GAPDH) expression and are presented as the fold-induction ($2^{-\Delta\Delta Ct}$) value for Ly6G$^{high}$Ly6C$^+$ MDSCs relative to Ly6G$^-$Ly6C$^+$ monocyte fraction.

In Vitro Macrophage and MDSC Experiments.

Ly6G$^{high}$Ly6C$^+$ MDSCs were isolated by FACS from S. aureus implant-associated tissues or spleens at day 14 after infection and bone marrow-derived macrophages were prepared, as previously reported (23). Cells were plated at $5\times10^4$ cells/well in a 96-well plate and stimulated with either peptidoglycan (PGN; 10 µg/ml) or heat-inactivated S. aureus ($10^7$/well) for 24 hours. After a 24-hour incubation period, supernatants were collected and stored at −80° C. until MILLIPLEX analysis.

Statistics.

Significant differences between experimental groups were determined by an unpaired two-tailed Student t-test or a one-way ANOVA with Bonferroni's multiple comparison post-hoc analysis using GraphPad Prism version 4 (LaJolla, Calif.). For all analyses, P<0.05 was considered statistically significant.

Example 2

Accumulation of CD11b$^+$Gr-1$^+$ Cells During S. aureus Orthopedic Biofilm infection.

Figure 2:
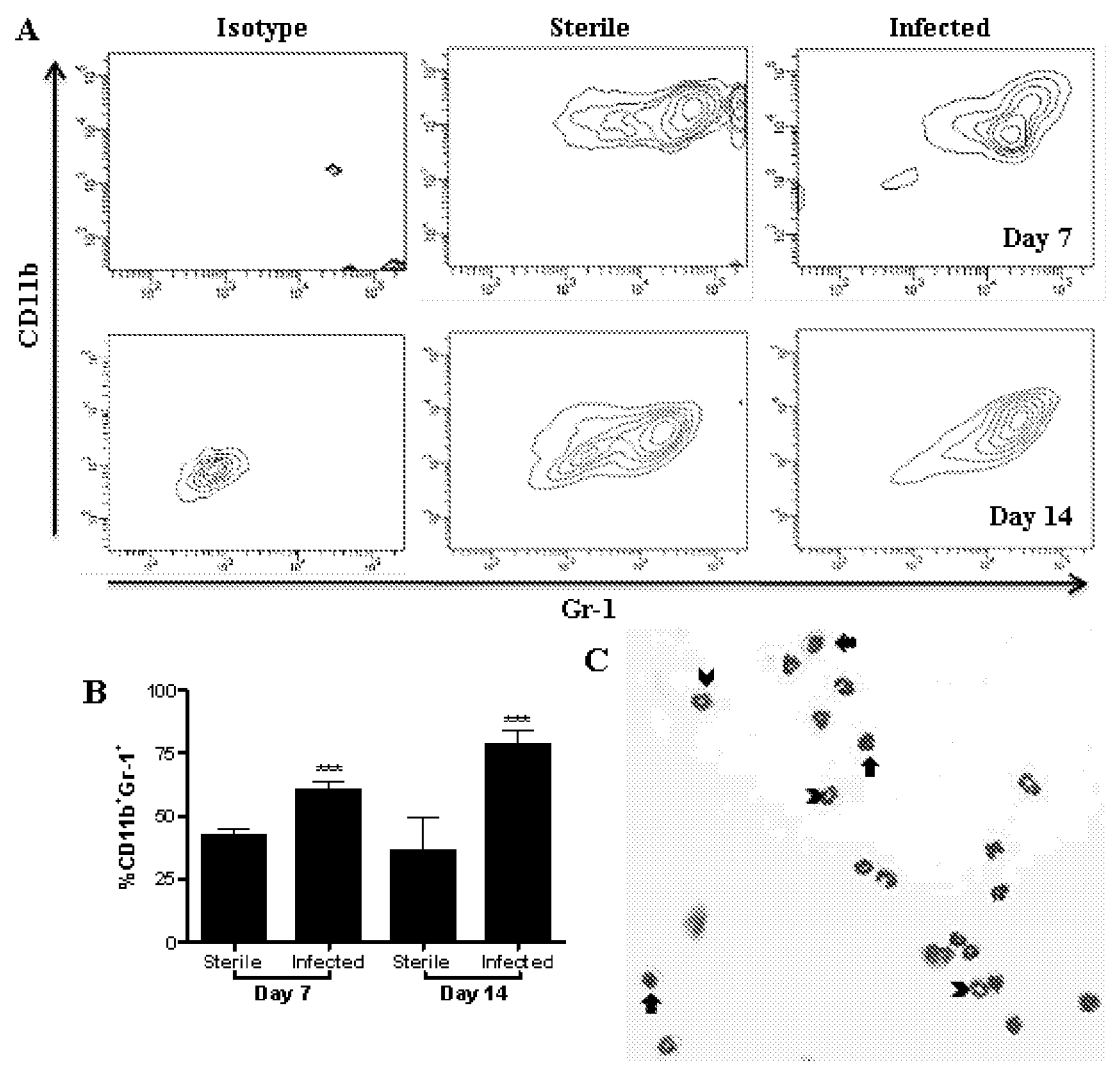
FIG. 2. Accumulation of CD11b⁺Gr-1⁺ cells during *S. aureus* orthopedic biofilm infection. Implant-associated tissues were collected from sterile and infected mice and analyzed by flow cytometry for CD11b⁺Gr-1⁺ cells at the indicated time points. (A) Representative contour plots and (B) CD11b⁺Gr-1⁺ infiltrates expressed as a percent of the total CD45⁺ leukocyte population. (C) Cytospin preparations of FACS-purified CD11b⁺Gr-1⁺ cells from infected tissues at day 14. Arrowheads and arrows indicate cells suggestive of immature granulocytes and monocytes, respectively. Significant differences are denoted by asterisks (***, p<0.001; unpaired two-tailed Student t-test) and are representative of 3 sterile and 5 infected mice per group.

S. aureus biofilms skew infiltrating macrophages towards an alternatively activated M2 state typified by Arg-1 expression (16, 24). However, Arg-1$^+$ cells distinct from macrophages were also observed, which led to an investigation of their identity. A likely candidate was MDSCs based on their robust Arg-1 expression and well-described anti-inflammatory attributes in cancer (2, 4, 5). Here, a mouse model of orthopedic biofilm infection (20) was used to demonstrate the presence and functional importance of MDSCs in shaping the anti-inflammatory biofilm milieu in an immunocompetent host. Biofilm formation on the orthopedic implant was confirmed by SEM, which revealed S. aureus attachment to a dense matrix deposited on the implant surface and bacterial tower formation (FIG. 1). A prominent CD11b$^+$Gr-1$^+$ infiltrate was observed, which accounted for approximately 75% of the total CD45$^+$ leukocyte population by day 14 after infection (FIGS. 2A and B). Co-expression of CD11b and Gr-1 is used to define MDSCs and cytospin preparations of FACS-purified CD11b$^+$Gr-1$^+$ cells recovered from the site of S. aureus biofilm infection confirmed their heterogeneous composition of both granulocytic and monocytic morphologies (FIG. 2C). In particular, cells with ringed nuclei suggested the presence of immature granulocytes, and immature monocytes with large rounded nuclei and little cytoplasm were also observed (FIG. 2C). CD11b$^+$Gr-1$^+$ cells were also detected in mice receiving sterile implants, which was not unexpected, because MDSCs have been reported in virtually every inflammatory environment and are associated with wound healing responses under normal conditions (19, 25). Their numbers, however, were significantly lower compared to S. aureus-infected animals (FIG. 2B). The abundance of CD11b$^+$Gr-1$^+$ cells during early S. aureus orthopedic infection may be one mechanism that contributes to the establishment of chronic disease.

Example 3

CD11b$^+$Gr-1$^+$ MDSCs Recruited to the Site of S. aureus Orthopedic Biofilm Infection Inhibit T Cell Activation.

A hallmark of MDSCs is their ability to inhibit antigen-specific and polyclonal T cell activation (4, 18). This is a critical attribute based on the promiscuity in surface marker expression between MDSCs and other myeloid lineages (25, 26). To determine whether S. aureus biofilm-associated CD11b$^+$Gr-1$^+$ infiltrates were bona fide MDSCs, their ability to inhibit polyclonal CD4$^+$ T cell activation was examined, because S. aureus immunodominant TCR epitopes have not yet been identified. MDSCs were recovered from tissues at day 14 post-infection, which coincided with maximum cell numbers at the infection site (FIG. 2B). CD11b$^+$Gr-1$^+$ cells from S. aureus-infected tissues significantly suppressed T cell proliferation (FIG. 3A), establishing their identity as MDSCs. The inhibitory activity of biofilm-associated MDSCs was further demonstrated by their ability to significantly impair T cell cytokine secretion, including TNF-α, IFN-γ, IL-17, and IL-4 (FIGS. 3B-E).

Also examined was whether the immunosuppressive nature of MDSCs was restricted to the biofilm infection site or if they were also suppressive in the periphery, which has been reported for MDSCs in tumor-bearing animals (27, 28). CD11b$^+$Gr-1$^+$ cells from the spleens of either naïve or infected animals were unable to suppress CD4$^+$ T cell proliferation. It was not unexpected that MDSCs from naïve animals failed to inhibit T cell activation, as pathologic conditions are known to elicit MDSC expansion and activation (2, 4, 29, 30). Several groups have reported that MDSCs only acquire suppressive function after exposure to factors in inflammatory environments (25, 27, 31) and the results disclosed herein indicate that these signals are only present within in the local biofilm milieu.

Figure 3:
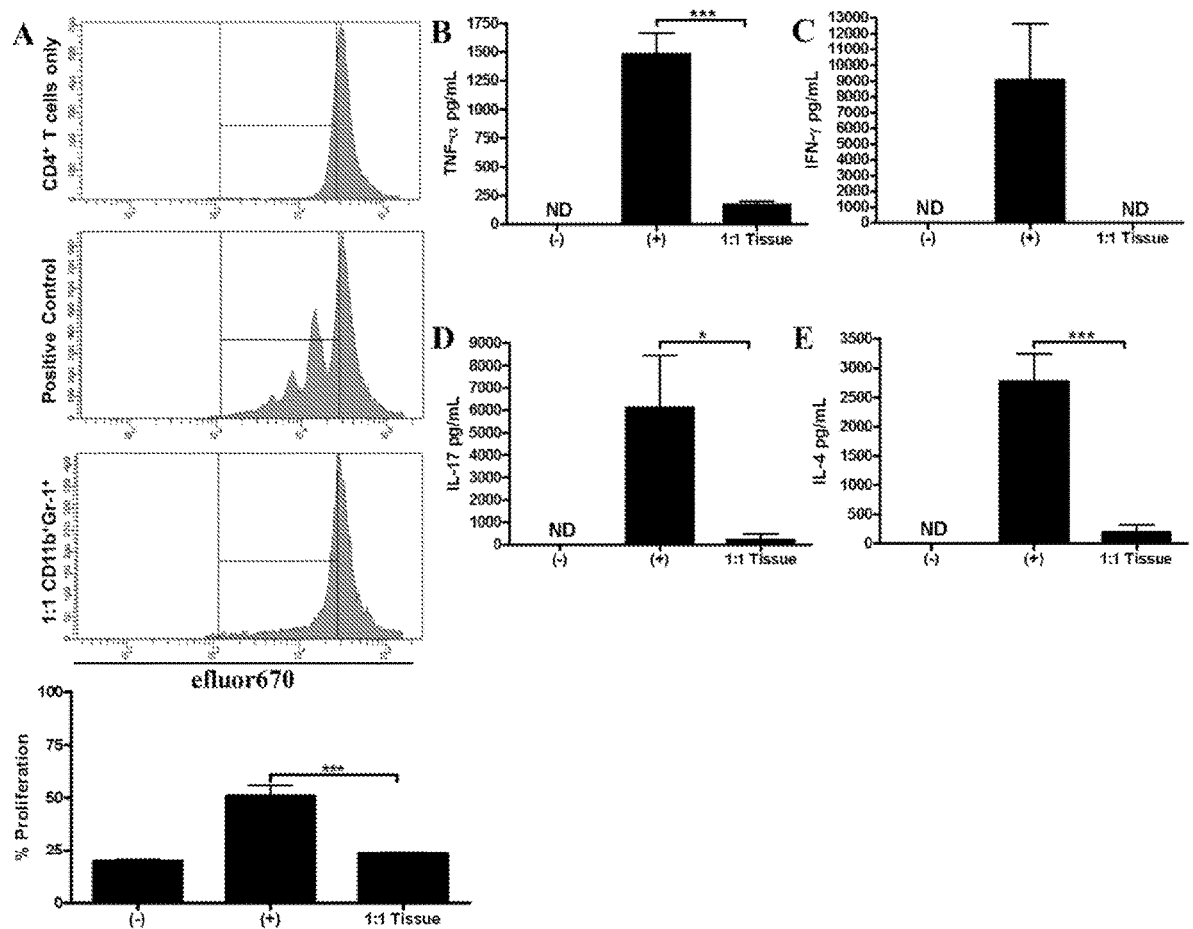
FIG. 3. CD11b$^+$Gr-1$^+$ infiltrates from the site of *S. aureus* biofilm infection inhibit T cell proliferation. FACS-purified CD11b$^+$Gr-1$^+$ cells recovered from infected joint tissues at day 14 were immediately cultured ex vivo with efluor670-labeled CD4$^+$ T cells at a 1:1 ratio for proliferation assays. (A) Representative histograms of fluorescence intensity, with percent proliferation reported. (B-E) Supernatants from MDSC-CD4$^+$ T cell co-cultures were collected at 72 hours to quantitate TNF-$\alpha$ (B), IFN-$\gamma$ (C), IL-17 (D), and IL-4 (E) by MILLIPLEX. Significant differences are denoted by asterisks (*, p<0.05; ***, p<0.001; unpaired two-tailed Student t-test). ND; Not detected; (−) T cells only; (+) T cells incubated with CD3/CD28 Dynabeads. Results are representative of three to nine independent experiments.
Figure 4:
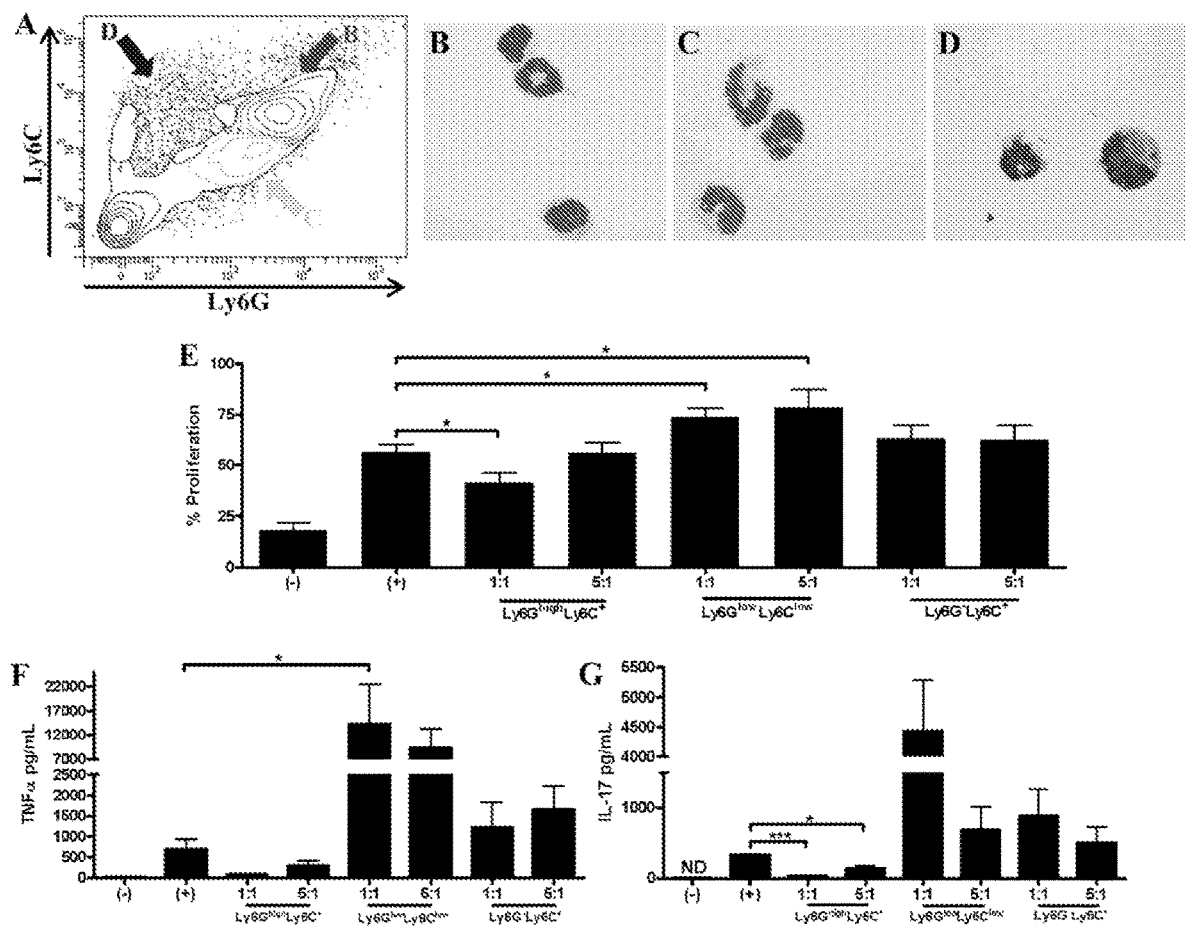
FIG. 4. Ly6G$^{high}$Ly6C$^+$ cells infiltrating *S. aureus* biofilms are bona fide MDSCs. Leukocyte infiltrates associated with *S. aureus*-infected joints were collected at day 14 and analyzed for Ly6C and Ly6G expression by flow cytometry. Representative contour plot (A) and cytospin preparations of FACS-purified Ly6G$^{high}$Ly6C$^+$ (B), Ly6G$^{low}$Ly6C$^{low}$ (C), and Ly6G$^-$Ly6C$^+$ (D) cells. (E) Analysis of ex vivo polyclonal CD4$^+$ T cell proliferation following a 1:1 and 1:5 co-culture with Ly6G$^{high}$Ly6C$^+$, Ly6G$^{low}$Ly6C$^{low}$, and Ly6G$^-$Ly6C$^+$ cells for 72 h, whereupon conditioned supernatants were assessed for TNF-$\alpha$ (F) and IL-17 (G) expression by MILLIPLEX. Significant differences are denoted by asterisks (*, p<0.05; ***, p<0.001; one-way ANOVA with Bonferroni's multiple comparison post-hoc analysis) and results are representative of three to nine replicates. ND, Not detected; (−) T cells only; (+) T cells incubated with CD3/CD28 Dynabeads.

Since the Gr-1 antibody RB6-C85 recognizes both Ly6G and Ly6C epitopes (32), staining for both markers was undertaken, which identified three distinct populations associated with S. aureus orthopedic biofilms, namely Ly6G$^{high}$Ly6C$^+$, Ly6G$^{low}$Ly6C$^{low}$, and Ly6G$^-$Ly6C$^+$ (FIG. 4A). Each subset was purified by FACS to determine which was responsible for the observed CD4$^+$ T cell suppression of the original Gr-1$^+$ population (FIG. 3). Ly6G$^{high}$Ly6C$^+$ cells significantly inhibited CD4$^+$ T cell proliferation in a ratio-dependent manner, confirming their identity as MDSCs (FIG. 4E). Similar to observations with the bulk CD11b$^+$Gr-1$^+$ population (FIG. 3), Ly6G$^{high}$Ly6C$^+$ cells decreased TNF-α and IL-17 expression (FIGS. 4F and G, respectively). Cytospins of the Ly6G$^{high}$Ly6C$^+$ population revealed an immature granulocytic morphology characterized by numerous ringed nuclei (FIG. 4B), which when taken together with their suppressive action, is indicative of G-MDSCs. The Ly6G⁻Ly6C⁺ population was typified by a relatively homogeneous monocyte-like morphology that was unable to suppress CD4⁺ T cell activation (FIGS. 4D and E), indicating these cells are inflammatory monocytes. Collectively, these results are the first to demonstrate the recruitment of a bona fide MDSC population in any model of staphylococcal infection or biofilm formation caused by any bacterial species.

Studies by other groups have reported neutrophil infiltrates in mouse models of S. aureus orthopedic infection (33-35). These reports, however, utilized either immunostaining with Ly6G, Ly6G depletion, or LysM-GFP mice to identify neutrophils, and these approaches cannot differentiate between neutrophils and MDSCs (36). It is possible that the Ly6G$^{low}$Ly6C$^{low}$ cells observed in the model of S. aureus orthopedic biofilm infection disclosed herein are neutrophils based on their cytospin morphology, revealing fewer immature cells compared to the MDSC population (FIGS. 4C and B, respectively), and lack of T cell suppressive activity (FIG. 4E).

Example 4

Ly6G$^{high}$Ly6C⁺ Cells Recruited to Sites of S. aureus Orthopedic Biofilm Infection Express Genes Characteristic of MDSCs.

Figure 5:
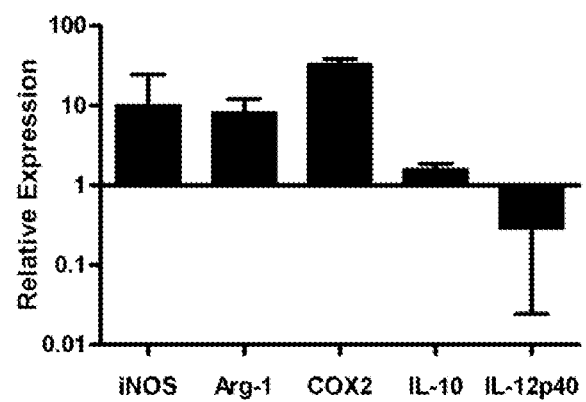
FIG. 5. Ly6G$^{high}$Ly6C$^+$ biofilm-associated infiltrates express genes characteristic of MDSCs. FACS-purified Ly6G$^{high}$Ly6C$^+$ MDSCs and Ly6G$^-$Ly6C$^+$ inflammatory monocytes were recovered from infected joint tissues at day 14, whereupon RNA was immediately isolated for qRT-PCR analysis. Gene expression levels in Ly6G$^{high}$Ly6C$^+$ MDSCs were calculated after normalizing signals against GAPDH and are presented as the fold-change relative to the Ly6G$^-$Ly6C$^+$ monocyte population. Results represent the mean±SEM of three independent experiments.

Due to the differential immunosuppressive properties of the Ly6G$^{high}$Ly6C⁺ and Ly6G⁻Ly6C⁺ subsets associated with S. aureus orthopedic biofilm infection, gene expression profiles of FACS-purified populations immediately ex vivo were examined by qRT-PCR as further confirmation of their identity. The Ly6G$^{high}$Ly6C⁺ MDSC subset displayed increased iNOS, Arg-1, COX-2, and IL-10 concomitant with reduced IL-12p40 expression compared to the Ly6G⁻Ly6C⁺ monocytic fraction (FIG. 5), similar to MDSC profiles described in other disease models (1, 37-40).

Figure 15:
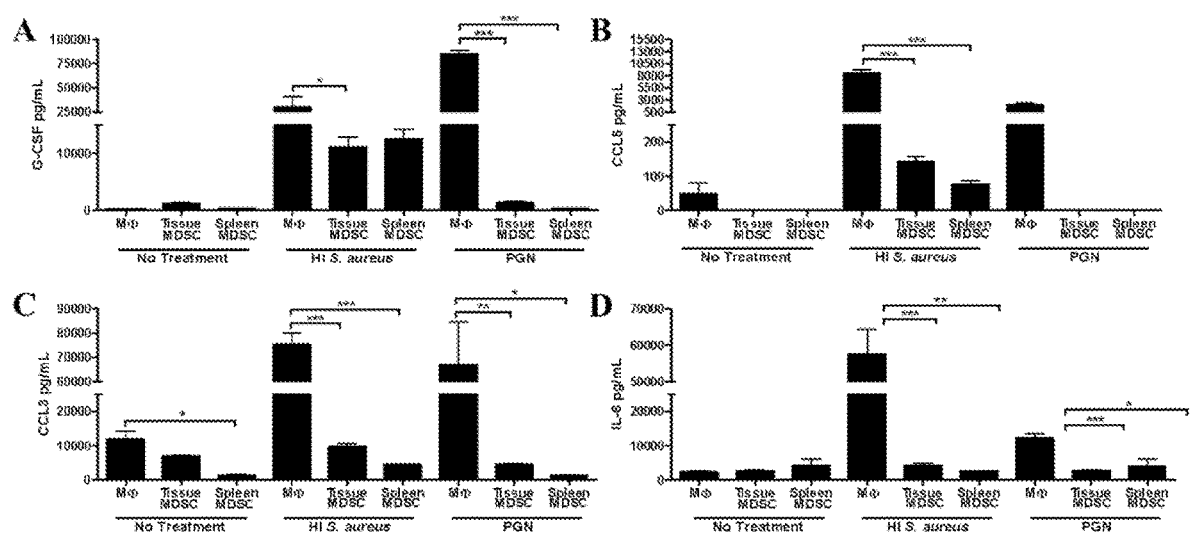
FIG. 15. MDSCs exhibit less inherent proinflammatory activity than macrophages. Bone marrow-derived macrophages (Mϕ) and FACS-purified $Ly6G^{high}Ly6C^+$ MDSCs recovered from the site of S. aureus orthopedic biofilm infection (tissue MDSC) or the spleen (spleen MDSC) of infected animals were stimulated with $10^7$ heat-inactivated (HI) S. aureus or PGN (10 µg/ml). Supernatants were collected at 24 h, whereupon G-CSF (A), CCL5 (B), CCL3 (C) and IL-6 (D) expression was quantitated by MILLIPLEX. Significant differences are denoted by asterisks (*, $p<0.05$; , $p<0.01$; *, $p<0.001$; one-way ANOVA with Bonferroni's multiple comparison post-hoc analysis) and are representative of three independent replicates.

MDSCs play an important role in regulating inflammatory processes through their production of several pro- and anti-inflammatory cytokines (7, 25). To assess the inflammatory status of MDSCs, cells were recovered from the site of biofilm infection or the spleen and immediately stimulated ex vivo with heat-inactivated S. aureus or peptidoglycan (PGN). Regardless of their origin, it was found that Ly6G$^{high}$Ly6C⁺ MDSCs were inherently less proinflammatory than macrophages (FIG. 15). Collectively, these results provide further evidence to support the identity of infiltrating Ly6G$^{high}$Ly6C⁺ cells into S. aureus orthopedic biofilm infections as MDSCs.

A cytokine that could play a significant role in immunoevasion by biofilm infections is the anti-inflammatory Interleukin 10 (IL-10). This cytokine is also known to have immunosuppressive properties. To assess the role that MDSCs might play in the production of IL-10, a transgenic mouse line harboring an IL-10-Green Fluorescent Protein fusion construct was used. The transgenic mouse line is available from the Jackson Laboratory (stock no. 014530) or it can be generated using conventional technologies. For this experiment, IL-10-GFP reporter mice were infected with 10³ CFU S. aureus USA300 LAC and sacrificed at days 3 and 5 post-infection, whereupon the percentages of IL-10-producing MDSCs (Ly6G$^{high}$Ly6C⁺), neutrophils (Ly6G$^{low}$Ly6C$^{low}$), monocytes (Ly6G⁻Ly6C⁺), and macrophages (F4/80⁺) in the soft tissue surrounding the knee were quantified by FACS. The CD45+ marker characteristic of leukocytes was stained and used to identify, by FACS, the MDSCs, neutrophils, monocytes and macrophages in the samples taken from the soft tissue surrounding the knee. The results showed that, at day 3, MDSCs constituted about 40% of leukocytes expressing GFP, neutrophils were about 4%, monocytes were about 4% and macrophages were about 8%. At day 5 post-infection, MDSCs were about 75% of leukocytes expressing GFP, with neutrophils at about 5%, monocytes at about 9% and macrophages at about 3%. Thus, MDSCs provide the major source of the immunosuppressive cytokine IL-10 during S. aureus biofilm infection. It is expected, moreover, that MDSCs are the major source of the immunosuppressive IL-10 contributing to the persistence of all biofilm infections, as there is no reason to expect a different role for the immune system for biofilm infections involving other microbes—the immune system functions at the level of recognizing all such infections as "foreign."

Example 5

Depletion of Ly6G⁺ MDSCs Increases Monocyte Infiltrates and their Intrinsic Proinflammatory Activity, Resulting in Enhanced S. aureus Biofilm Clearance.

Figure 6:
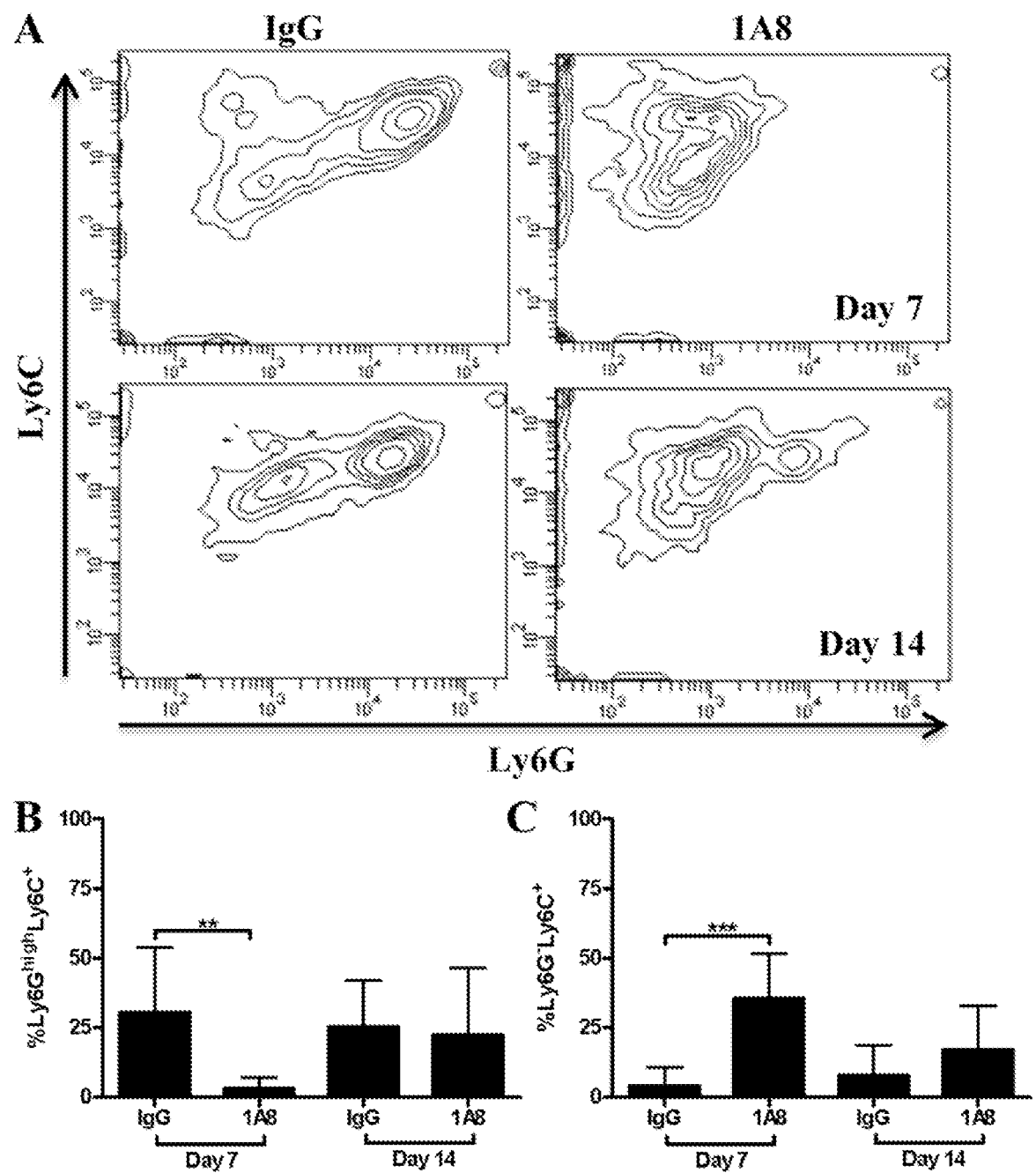
FIG. 6. MDSC depletion augments monocyte recruitment during *S. aureus* orthopedic biofilm infection. Implant-associated tissues from 1A8- and isotype control-treated mice were collected at the indicated time points after infection and analyzed by flow cytometry. (A) Representative contour plots of Ly6C and Ly6G staining and (B) quantitation of Ly6G$^+$Ly6C$^+$ MDSCs and (C) Ly6C$^+$ inflammatory monocytes. Results are presented as a percentage of the total CD45$^+$ leukocyte infiltrate and are representative of two independent experiments (n=10 mice per group). Significant differences are denoted by asterisks (, p<0.01; *, p<0.001; unpaired two-tailed Student t-test).
Figure 7:
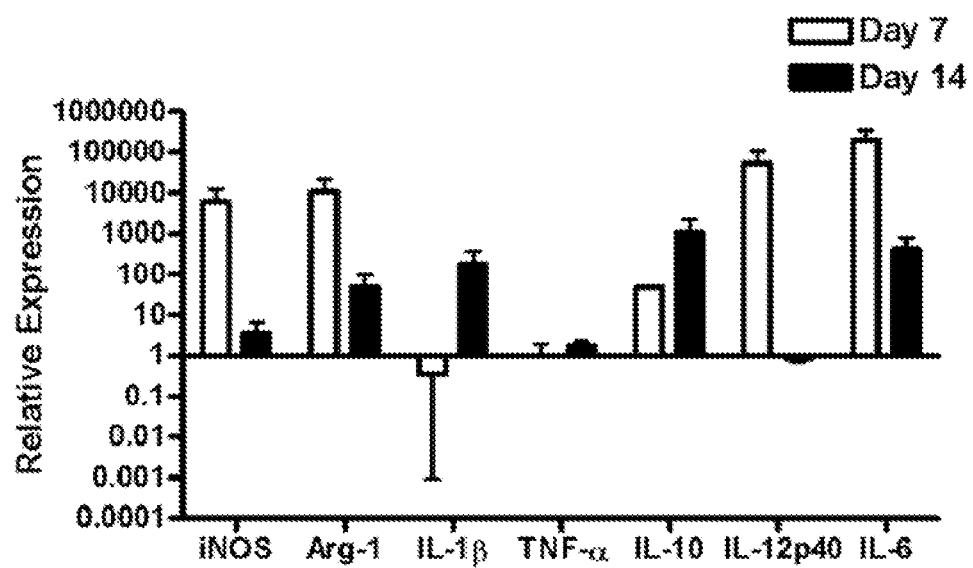
FIG. 7. MDSC depletion enhances intrinsic proinflammatory gene expression in Ly6C$^+$ monocytes during *S. aureus* biofilm infection. Ly6G$^-$Ly6C$^+$ monocytes were purified from tissues surrounding the infected joints of 1A8- and isotype control-treated mice at days 7 and 14 post-infection by FACS, whereupon RNA was immediately isolated for qRT-PCR analysis. Gene expression levels in Ly6G$^-$Ly6C$^+$ monocytes recovered from MDSC depleted animals were calculated after normalizing signals against GAPDH and are presented as the fold-change relative to Ly6G$^-$Ly6C$^+$ cells from isotype control mice. Results represent the mean±SEM of two independent experiments.

To assess the functional role of Ly6G$^{high}$Ly6C⁺ MDSCs in orchestrating the anti-inflammatory biofilm milieu to facilitate bacterial persistence, mice were treated with the monoclonal antibody 1A8 to target Ly6G⁺ cells (37, 41, 42). This approach would deplete MDSCs, leaving the Ly6C⁺ monocyte and macrophage populations intact and able to combat S. aureus infection, presumably in the absence of immunosuppression. It was confirmed that 1A8 was effective at depleting the Ly6G$^{high}$Ly6C⁺ MDSC population, which was more robust at day 7 compared to day 14 (FIGS. 6A and B). Interestingly, the frequency of Ly6C⁺ monocytes was significantly increased at day 7 (FIG. 6C) and the absence of immunosuppressive Ly6G⁺ MDSCs was expected to promote the proinflammatory attributes of these Ly6C⁺ mononuclear phagocytes. To address this possibility, the activation state of FACS-purified Ly6G⁻Ly6C⁺ cells from the infection site of 1A8-treated, versus isotype control, mice was examined by qRT-PCR. In the context of MDSC depletion with 1A8, iNOS, IL-12p40, and IL-6 expression was increased in Ly6G⁻Ly6C⁺ cells at day 7 (FIG. 7). Increased Arg-1 and IL-10 expression was also observed in Ly6G⁻Ly6C⁺ cells (FIG. 7) and although both possess anti-inflammatory properties, they may be important in maintaining a balanced inflammatory environment at the site of infection, due to the absence of normally immunosuppressive MDSCs.

Figure 8:
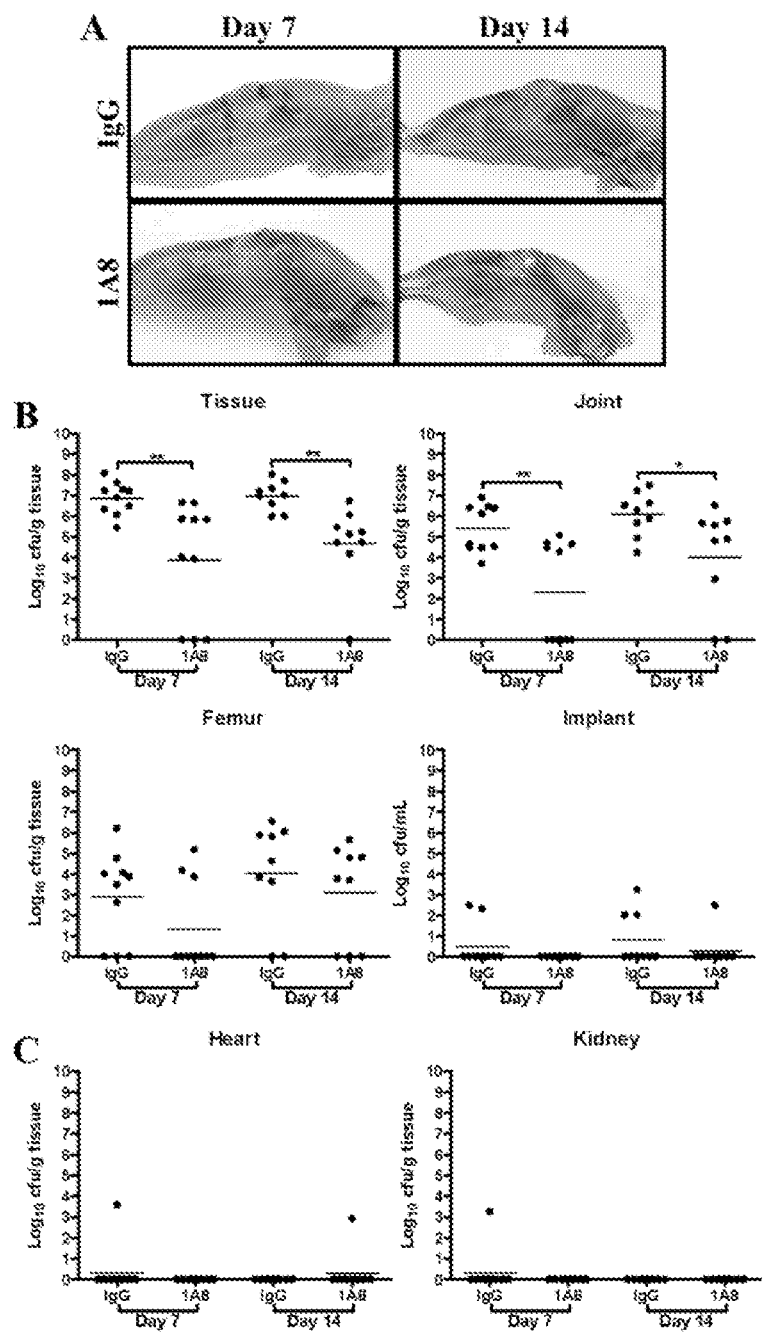
FIG. 8. MDSC depletion reduces *S. aureus* burdens during orthopedic biofilm infection. (A) Gross appearance of infected tissues from animals receiving 1A8 or an isotype-matched IgG. (B) Bacterial burdens associated with the knee joint, surrounding soft tissue, femur, and orthopedic implant and (C) heart and kidney of IgG control or 1A8-treated animals at days 7 and 14 post-infection. Results are expressed as the number of CFU per ml for orthopedic implants or CFU per gram tissue to correct for alterations in tissue sampling sizes. Significant differences in bacterial burdens between IgG and 1A8-treated mice are denoted by asterisks (*p<0.05; **, p<0.01; unpaired two-tailed Student t-test).

Because Ly6C⁺ monocyte infiltrates were increased in the context of MDSC depletion and displayed intrinsic proinflammatory activity, next examined was whether this would translate into superior anti-biofilm activity. This expectation was confirmed, because Ly6G⁺ cell depletion with 1A8 significantly reduced S. aureus burdens in both the tissue and knee joint at days 7 and 14 post-infection compared to isotype control animals (FIG. 8B), which correlated with less gross evidence of exudate formation in MDSC-depleted mice (FIG. 8A). Ly6G⁺ cell depletion did not cause S. aureus dissemination from the primary site of infection (FIG. 8C) and histopathologic analysis of H&E-stained tissues showed no dramatic differences in the degree of joint inflammation or splenic architecture (as a measure of extramedullary hematopoiesis) between 1A8-treated and isotype control animals.

Figure 9:
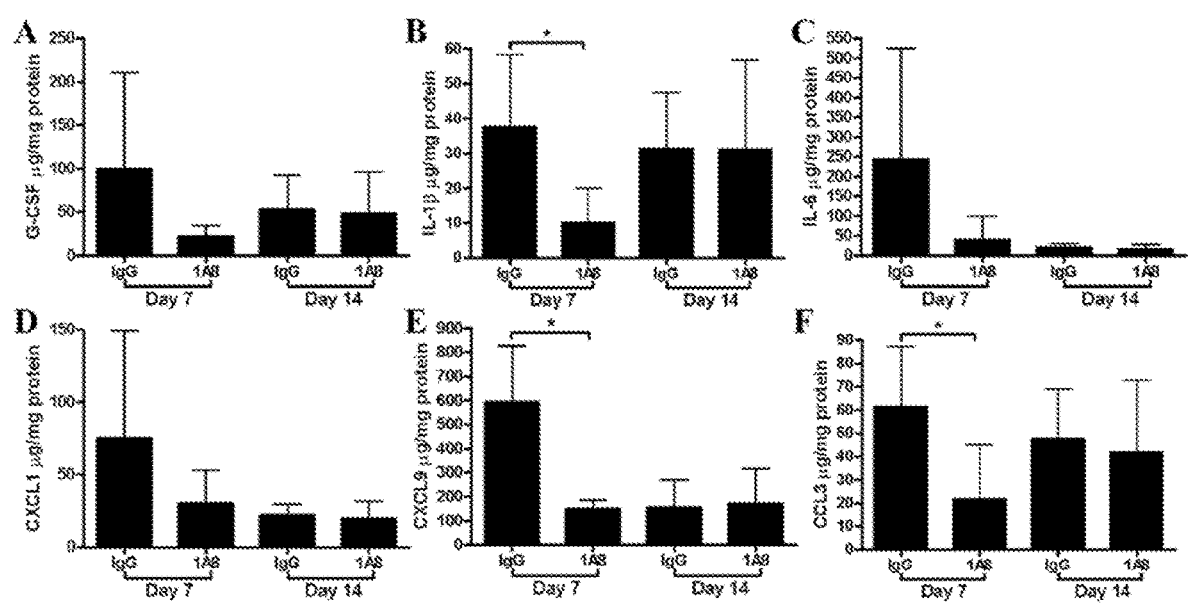
FIG. 9. 1A8 treatment attenuates inflammatory mediator production during *S. aureus* orthopedic biofilm infection. Tissue homogenates surrounding orthopedic implants were prepared at days 7 and 14 post-infection from 1A8- and isotype control-treated mice, whereupon G-CSF (A), IL-1$\beta$ (B), IL-6 (C), CXCL1 (D), CXCL9 (E) and CCL3 (F) expression was quantitated by MILLIPLEX. Results were normalized to the amount of total protein recovered to correct for alterations in tissue sampling size. Significant differences are denoted by asterisks (*, p<0.05; unpaired two-tailed Student t-test) and are representative of five mice per group.

To investigate the impact of Ly6G⁺ cell depletion on the inflammatory milieu during S. aureus orthopedic biofilm infection, soft tissues surrounding the knee, the knee joint itself, and a femur were analyzed using MILLIPLEX arrays. Levels of several cytokines (G-CSF, IL-1β, IL-6) and chemokines (CXCL1, CXCL9 and CCL3) were dramatically reduced in 1A8-treated, compared to isotype control, mice primarily at day 7 (FIG. 9), in agreement with increased bacterial clearance in the former (FIG. 8B). Collectively, these results demonstrate that during *S. aureus* orthopedic biofilm infection, Ly6G$^{high}$Ly6C$^+$ MDSCs elicit a local microenvironment that restricts monocyte/macrophage proinflammatory activity, facilitating the establishment of an anti-inflammatory milieu that favors bacterial persistence. It was expected that these effects would not be significantly influenced by neutrophil loss following 1A8 treatment, because the majority of Ly6G$^+$ leukocytes infiltrating infected joints (i.e., about 75%) were MDSCs, and the data confirmed this expectation.

Having shown that MDSCs maintained an immunosuppressive, anti-inflammatory environment conducive to persistent biofilm infection, and that removal of these cells promoted microbe clearance, an experiment was designed to determine how MDSC levels are controlled. More particularly, the mouse model was again used, this time to assess the role that IL-10 might have in maintaining and/or recruiting MDSCs to biofilm infection sites over time. IL-10 knockout (KO) and wild-type (WT) mice were infected with $10^3$ CFU *S. aureus* USA300 LAC and sacrificed at post-infection days 3, 7, and 14, whereupon percentages of MDSCs (Ly6G$^{high}$Ly6C$^+$), neutrophils (Ly6G$^{low}$Ly6C$^{low}$), monocytes (Ly6G$^-$Ly6C$^+$), and macrophages (F4/80$^+$) were quantitated by FACS. A comparison of WT and corresponding IL-10 KO cells showed significant changes in relative cell levels at day 14 post-infection for MDSCs, monocytes and macrophages. For MDSCs, WT and IL-10 KO cells were at equivalent levels at days 3 (about 70% of leukocytes) and 7 (about 55% of leukocytes) post-infection, but at day 14 post-infection, wild-type MDSCs remained in excess of 50% of all leukocytes while IL-10 KO MDSCs fell from over 50% to about 13%, a relative 4-fold decrease.

The situation with macrophages was different in that the significant change in relative numbers of WT macrophages versus IL-10 KO macrophages was attributable to a decline in WT macrophage levels, from about 8% to less than 1% of leukocytes, while IL-10 KO macrophage levels remained relatively constant at about 5%. The relative changes in monocyte levels also reflected a slight increase in the numbers of IL-10 KO monocytes relative to WT monocytes at day 14 post-infection. At day 3 post-infection, WT and IL-10 KO monocytes each were about 8% of leukocytes; at day 14 post-infection, WT cells remained at about 8% but IL-10 KO cells increased to represent 15% of all leukocytes. Neutrophils showed a slight decline in both WT and IL-10 KO cells comparing day 3 post-infection (each about 12%) to day 14 post-infection (each about 8%). Thus, loss of IL-10 led to a dramatic reduction in MDSCs at the site of biofilm infection, while having little effect on neutrophils and a modest but statistically significant stimulatory effect on monocytes and macrophages. Based on these data, it is apparent that IL-10 is important for MDSC recruitment during later stages of biofilm infection, such as *S. aureus* biofilm infection.

Example 6

Loss of MDSCs is Associated with Clearance of Biofilm Infections

Example 5 showed that the absence of the immunosuppressive and anti-inflammatory cytokine IL-10 resulted in a dramatic and selective reduction in the numbers of MDSCs, but not monocytes, macrophages or neutrophils. An experiment was then designed to assess the effect on biofilm infection of the loss of IL-10, now known to lead to a reduction in MDSC infiltrates. In particular, IL-10 knockout (KO) and wild-type (WT) mice were infected with $10^3$ CFU *S. aureus* USA300 LAC and sacrificed at post-infection day 3, 7, or 14, whereupon bacterial burdens in the soft tissue surrounding the knee, the knee joint itself, a femur, and an implant (see Example 1) were determined. In the soft tissue surrounding the knee region, bacterial burdens in WT and IL-10 KO mice were equivalent at about $6 \times 10^7$ cfu *S. aureus* per gram of tissue. At day 3, there was a statistically insignificant decrease in IL-10 KO biofilm burdens relative to WT animals, while at day 14 post-infection, bacterial burdens in WT mice held relatively steady at about $10^7$ cfu/gram tissue, while IL-10 KO titers dropped to about $7 \times 10^4$ cfu/gram tissue, a difference significant at the $p < 0.001$ level.

In the knee joint itself, WT and IL-10 KO biofilm burdens were equivalent at about $7 \times 10^6$ at day 3, but at day 7, WT cell levels remained constant while IL-10 KO titers dropped to $10^5$ cells/gram tissue, a relative reduction of statistical significance at the $p < 0.05$ level. In the femur, WT biofilm burdens ranged around $5 \times 10^4$ to $5 \times 10^5$ cfu/gram, but IL-10 KO titers steadily fell from $2 \times 10^5$ cfu/gram at day 3 post-infection to about $7 \times 10^3$ cfu/gram at 7 days post-infection and down to about $10^2$ cfu/gram at day 14 post-infection. The differences in biofilm burdens in WT versus IL-10 KO mice were significant at the $p < 0.01$ level by day 7 post-infection and at the $P < 0.001$ level by day 14 post-infection. Finally, for the implant, biofilm burdens were at about 20-40 cfu/ml of sample at day 3 post-infection. By post-infection day 7, WT animals had just under $10^3$ cfu/ml while IL-10 KO mice were at about 5 cfu/ml, a statistically significant difference at the $p < 0.05$ level. By day 14 post-infection, however, biofilm burdens in both backgrounds had dropped, with WT MDSCs at about 7 cfu/ml and IL-10 KO MDSCs at 0 cfu/ml.

Reduction in the level of IL-10, shown to lead to a lower level of MDSCs (Example 5), also leads to a reduction in biofilm infection burden, as shown by the experiment described in this Example, where a *S. aureus* biofilm infection associated with each of a soft tissue surrounding a joint, a joint (the knee) itself, a bone (the femur), and a prosthetic or artificial device (the implant) was shown to be reduced over time in an IL-10 KO mouse versus a WT mouse. Thus, it is expected that reducing, eliminating, or preventing IL-10 expression or activity is/are suitable for methods of reducing an MDSC level, and for methods of preventing, treating or ameliorating a biofilm infection.

Having shown that IL-10 loss led to a reduction in MDSC levels and that this observation could be extended to a reduction in biofilm infection burden, an experiment was designed and conducted to elucidate any effect of IL-10 loss on cytokine signaling. Again, IL-10 knockout (KO) and wild type (WT) mice were infected with $10^3$ CFU *S. aureus* USA300 LAC and sacrificed at days 7 and 14 post-infection, whereupon cytokine assays using MILLIPLEX arrays were performed. In particular, G-CSF, IL-1β, IL-6, IL-9, MIP-1α, and MIG were subjected to quantitative assay using a Milliplex array. The results showed that, for all pro-inflammatory cytokines except IL-9, loss of IL-10 and a reduction/loss of biofilm burden led to a relative reduction in pro-inflammatory cytokines (G-CSF, IL-1β, MIP-1α, and MIG). For IL-6, there was a slight increase over time, but the increase was only significant at $p < 0.05$. IL-9 levels increased about three-fold over time in the IL-10 KO background relative to the WT background, and this change, like the reductions in the four cytokines noted above, was significant at the p<0.001 level. These results show that, in general, loss of IL-10, and a reduction in biofilm infection burden, is associated with reduced inflammatory mediator production, consistent with the results disclosed elsewhere herein that MDSCs play a significant role in maintaining biofilm infections in a persistent state, and that MDSCs yield this result, at least in part, through the production of IL-10.

Having shown that IL-10 KO mice display significant reductions in MDSC infiltrates that coincide with reduced biofilm burdens, direct demonstration that MDSCs were responsible for these outcomes was demonstrated by the adoptive transfer of WT MDSCs into orthopedic infections of IL-10 KO mice. Direct evidence of MDSCs as being responsible for promoting biofilm formation was shown by the ability of adoptively transferred WT MDSCs to restore bacterial burdens in IL-10 KO mice to those observed in WT animals. Specifically, at day 14 post-infection, in the soft tissue surrounding the knee region, bacterial burdens in WT mice were about $10^7$ cfu/gram tissue, while IL-10 KO titers dropped to about $5 \times 10^5$ cfu/gram tissue, a difference significant at the p<0.05 level. Thus, adoptive transfer of WT MDSCs into IL-10 KO mice restored biofilm levels to that observed in WT animals at about $10^7$ cfu/gram tissue.

In the knee joint itself, biofilm burdens in WT mice were about $10^7$ cfu/gram tissue, while IL-10 KO titers dropped to about $5 \times 10^5$ cfu/gram tissue, a difference significant at the p<0.01 level. Adoptive transfer of WT MDSCs into IL-10 KO mice restored biofilm levels to that observed in WT animals at about $5 \times 10^6$ cfu/gram tissue.

Example 7

Figure 10:
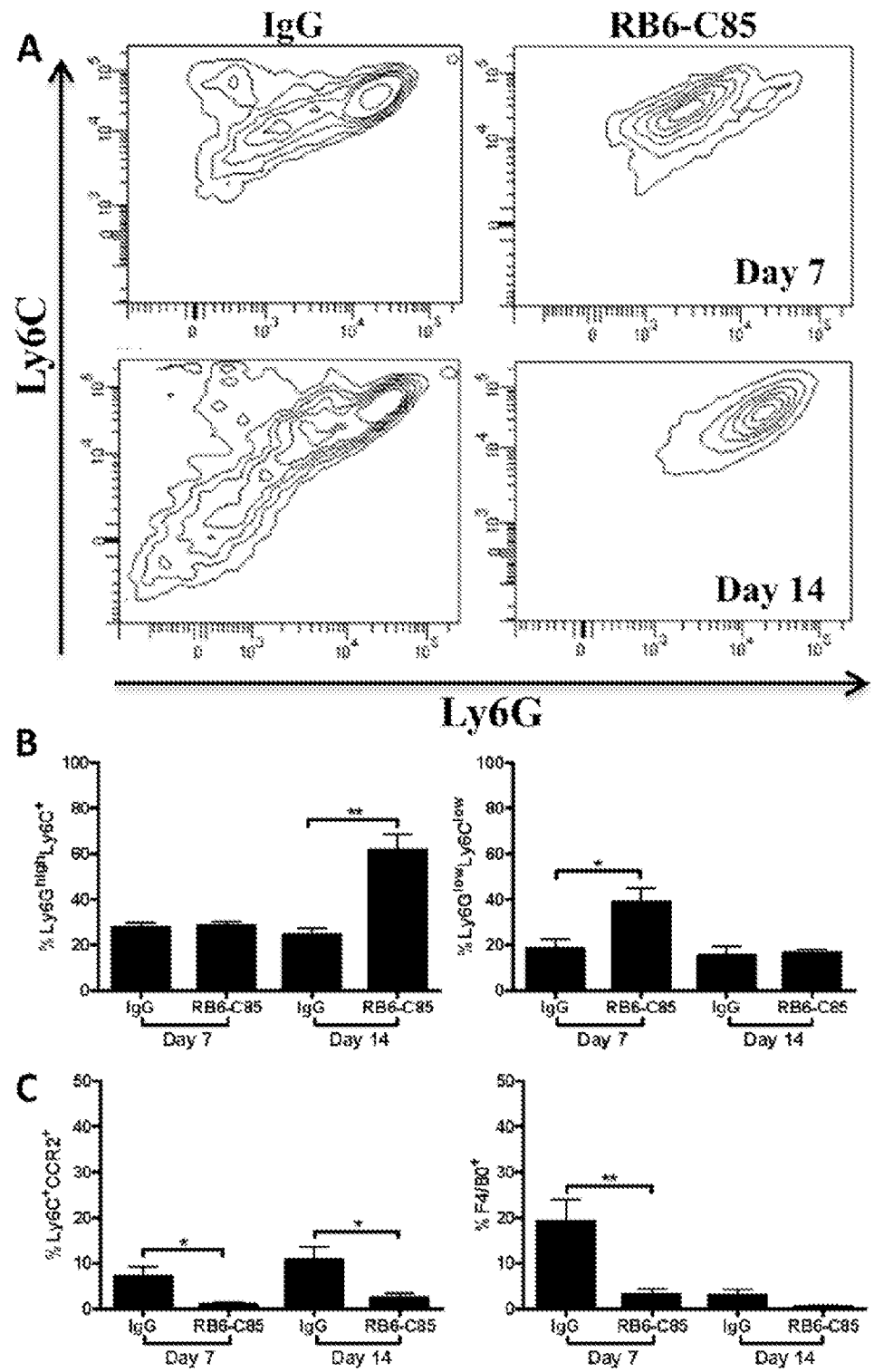
FIG. 10. RB6-C85 administration alters leukocyte infiltrates during *S. aureus* orthopedic biofilm infection. Implant-associated tissues from RB6-C85- and isotype control-treated mice were collected at the indicated time points after infection and analyzed by flow cytometry. (A) Representative contour plots of Ly6C and Ly6G staining and quantitation of (B) Ly6G$^{high}$Ly6C$^+$ MDSCs and Ly6G$^{low}$Ly6C$^{low}$ neutrophils and (C) inflammatory monocytes (CCR2$^+$) and macrophages (F4/80$^+$) present in infected animals receiving RB6-C85 or isotype control antibody. Results are expressed as a percent of the total CD45$^+$ leukocyte population. Significant differences are denoted by asterisks (*, p<0.05; **, p<0.01; unpaired two-tailed Student t-test) and are representative of 10 mice per group from two independent experiments.
Figure 11:
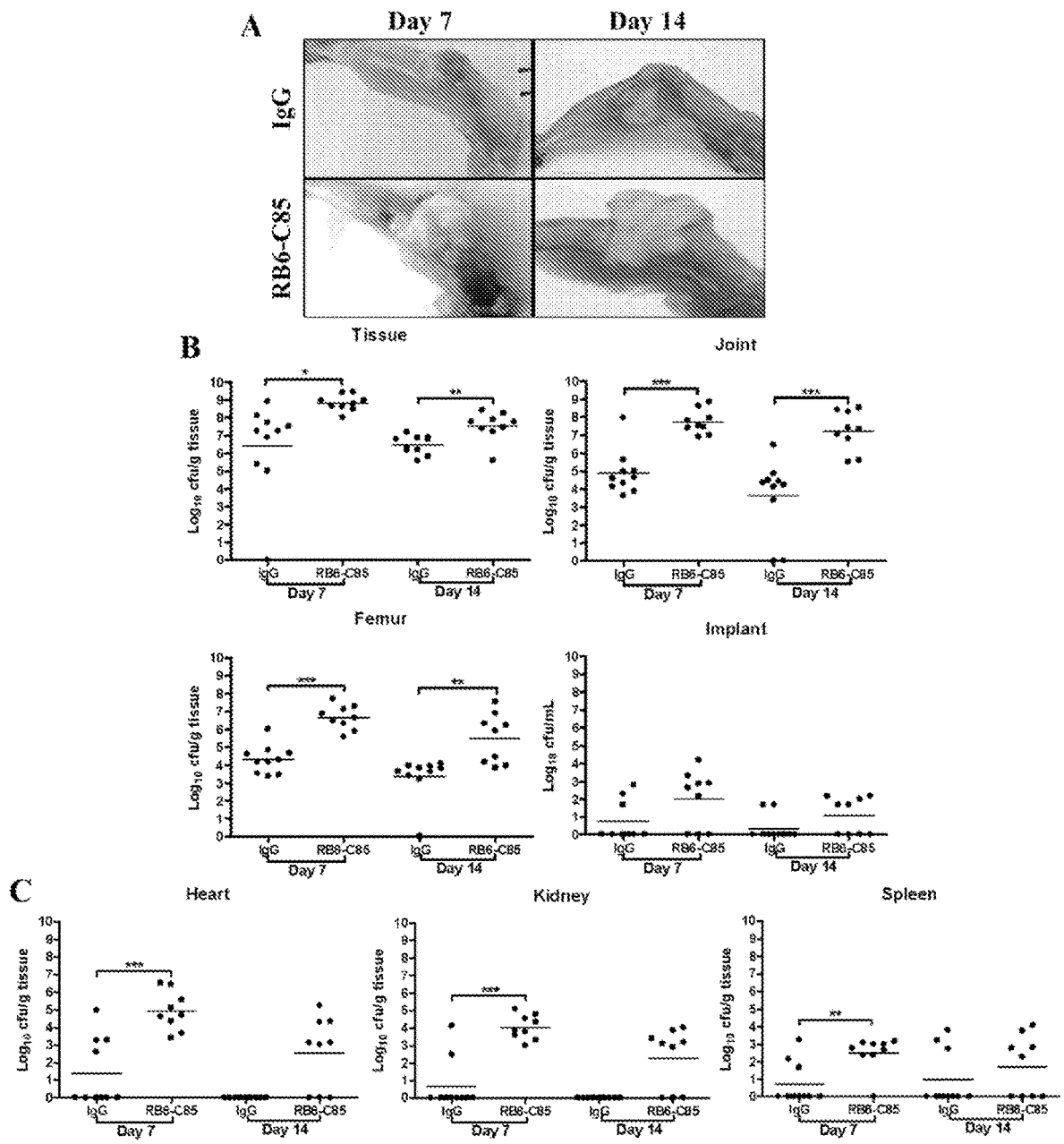
FIG. 11. RB6-C85 treatment enhances *S. aureus* biofilm burdens and dissemination. (A) Gross appearance of infected tissues from animals receiving RB6-C85 or an isotype-matched IgG revealed a marked caseous exudate in the former. (B) Bacterial burdens associated with the knee joint, surrounding soft tissue, femur, and orthopedic implant and (C) heart, kidney and spleen of control IgG or RB6-C85-treated animals at days 7 and 14 post-infection. Results are expressed as CFU per ml for orthopedic implants or CFU per gram of tissue to correct for differences in tissue sampling size. Significant differences between IgG and RB6-C85 animals are denoted by asterisks (*p<0.05; , p<0.01; *, p<0.001; unpaired two-tailed Student t-test) and are representative of 10 mice per group from two independent experiments.
Figure 16:
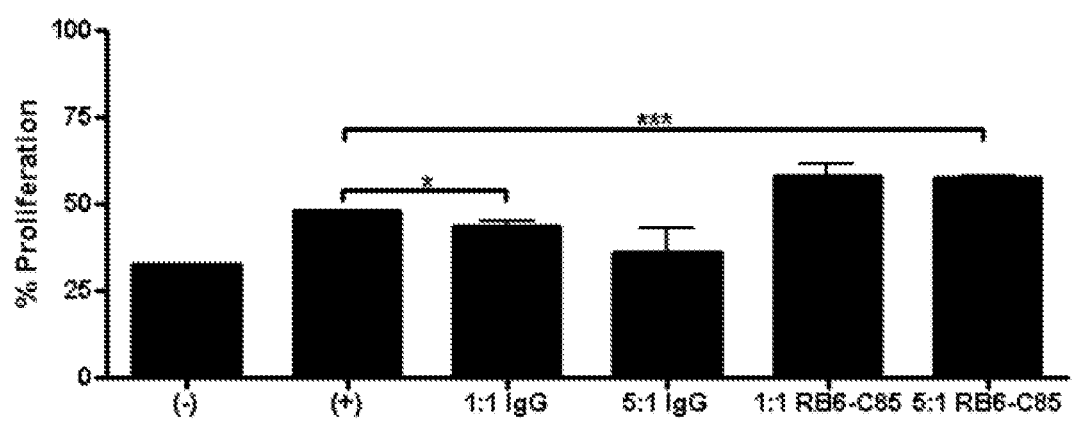
FIG. 16. The $Ly6G^{high}Ly6C^+$ infiltrate observed during Gr-1 depletion does not suppress T cell proliferation. FACS-purified $Ly6G^{high}Ly6C^+$ cells recovered from infected joint tissues of mice treated with RB6-C85 (Gr-1) or isotype-matched control IgG at day 14 were immediately cultured ex vivo with efluor670-labeled $CD4^+$ T cells for proliferation assays at either a 1:1 or 5:1 ratio [(−) T cells only; (+) T cells incubated with CD3/CD28 Dynabeads]. Results are representative of two independent replicates with significant differences denoted by asterisks (*, $p<0.05$; ***, $p<0.001$; one-way ANOVA with Bonferroni's multiple comparison post-hoc analysis).

Gr-1$^+$ Cell Depletion Confirms the Inhibitory Action of MDSCs on Monocytes/Macrophages to Prevent S. aureus Biofilm Clearance The results disclosed herein have established that MDSC depletion with 1A8 facilitated S. aureus biofilm clearance, in part, due to decreased immunosuppressive effects that promoted the proinflammatory attributes of infiltrating monocytes and macrophages. To further demonstrate that monocytes/macrophages were critical for anti-biofilm activity in the absence of an MDSC infiltrate, mice were treated with the monoclonal antibody RB6-C85. Similar to 1A8, RB6-C85 depletes Ly6G$^+$ MDSCs and neutrophils, but also targets monocytes based on its reactivity with Ly6C, which would also impact macrophage numbers by default (29, 37, 41-43). Therefore, any differences between 1A8 and RB6-C85 depletion would further support a role for monocytes/macrophages in mediating biofilm clearance without the suppressive MDSC population. As previously demonstrated, Ly6G/Ly6C staining detected three cell populations in implant-associated tissues of isotype control animals at days 7 and 14 following infection, namely Ly6G$^{high}$Ly6C$^+$ MDSCs, a Ly6G$^{low}$Ly6C$^{low}$ granulocyte-like population, and a Ly6G$^-$Ly6C$^+$ inflammatory monocyte subset (FIG. 10A). At day 7 post-infection, however, RB6-C85-treated animals only displayed one cell population that shifted from Ly6G$^{low}$Ly6C$^{low}$ to Ly6G$^{high}$Ly6C$^+$ at day 14 after infection (FIG. 10B). The percentage of Ly6G$^{low}$Ly6C$^{low}$ cells in RB6-C85-treated animals was significantly higher than isotype-treated controls at day 7 post-infection; however, no differences were apparent at day 14, because the population had shifted to Ly6G$^{high}$Ly6C$^+$ (FIG. 10B). Although Ly6G$^{high}$Ly6C$^+$ infiltrates were increased in RB6-C85-treated animals at day 14 post-infection (FIG. 10B), they were unable to inhibit T cell proliferation (FIG. 16) and, as such, do not represent a true MDSC phenotype. Therefore, it is expected that the presence of Ly6G$^{low}$Ly6C$^{low}$ and Ly6G$^{high}$Ly6C$^+$ populations in the infected joint of RB6-C85-treated mice results from increased demand from the overwhelming infection (FIG. 11), which agrees with the results to follow demonstrating extensive extramedullary hematopoiesis in the spleens of these animals. This is supported by the finding that Ly-6G$^+$Ly-6C$^+$ cells were significantly lower in RB6-C85-treated mice receiving sterile implants compared to isotype control antibody.

Also examined were CCR2 and F4/80 expression as markers for inflammatory monocytes and macrophages, respectively (44-46). Because RB6-C85 also recognizes the Ly6C epitope, it was expected that both of these cell populations would be decreased, as CCR2$^+$ inflammatory monocytes express Ly6C and differentiate into F4/80$^+$ macrophages once they have migrated into tissues (45). As expected, the percentage of Ly6C$^+$CCR2$^+$ cells was significantly decreased in RB6-C85-treated animals compared to isotype controls at days 7 and 14 after infection (FIG. 10C) Likewise, there were significantly fewer F4/80$^+$ macrophages in RB6-C85-depleted mice at day 7 post-infection, and only a very small percentage of cells remained at day 14 (FIG. 10C).

Example 8

Figure 12:
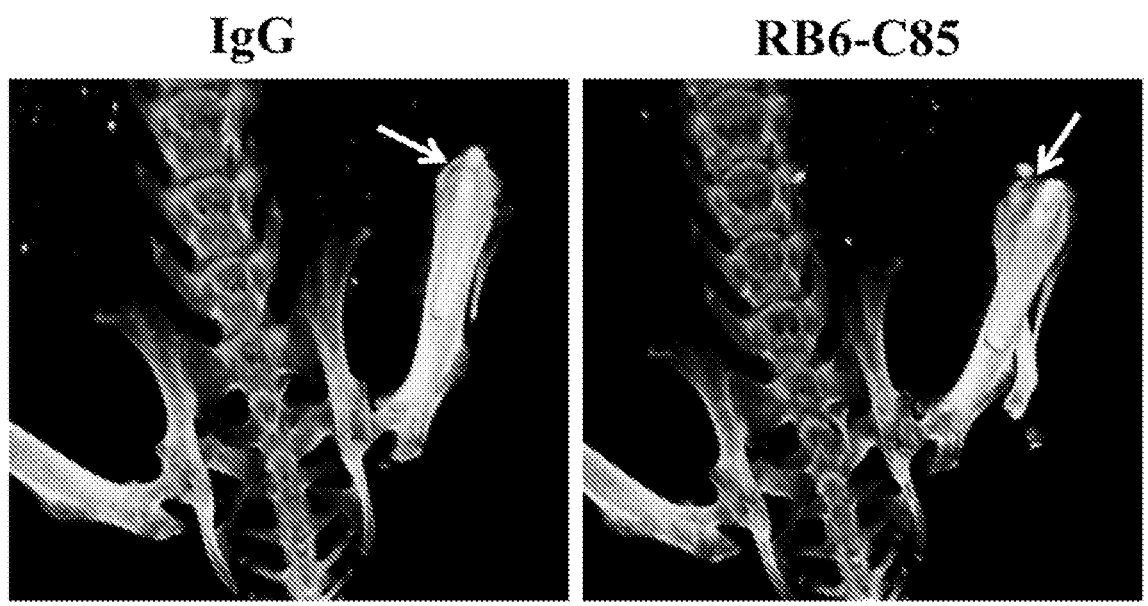
FIG. 12. RB6-C85 administration results in increased osteolysis during *S. aureus* orthopedic biofilm infection. CT images (dorsal view) are presented at day 14 post-infection from mice receiving RB6-C85 or isotype control Antibody. Arrows indicate the region of bone loss near the implant tip at the patella. Color intensity is indicative of bone density, where white=most dense, dark orange=least dense. Images are representative of 4 individual animals per group.

Gr-1$^+$ Cell Depletion Exacerbates S. aureus Orthopedic Biofilm Infection Due to the Loss of Monocyte/Macrophage Effectors Strikingly, S. aureus-infected mice treated with RB6-C85 displayed a grossly visible caseous exudate (FIG. 11A), which was typified by significantly increased bacterial burdens in the knee joint, surrounding soft tissue, and femur at days 7 and 14 after infection compared to infected animals receiving an isotype-matched control antibody (FIG. 11B). Histological analysis of tissues collected from RB6-C85-treated mice revealed increased inflammation in the joint space, surrounding soft tissue, and bone compared to isotype control animals (Table 1). Furthermore, the degree of osteolysis was more severe in RB6-C85-treated animals, as evidenced by CT imaging (FIG. 12) and femurs were more brittle upon harvest. These results are in stark contrast with those obtained during 1A8 depletion, where biofilm burdens were reduced, indicating monocytes and macrophages are able to promote bacterial clearance in the absence of an immunosuppressive MDSC population, since the only difference between the antibody-depletion strategies was the targeting of monocytes/macrophages.

Figure 13:
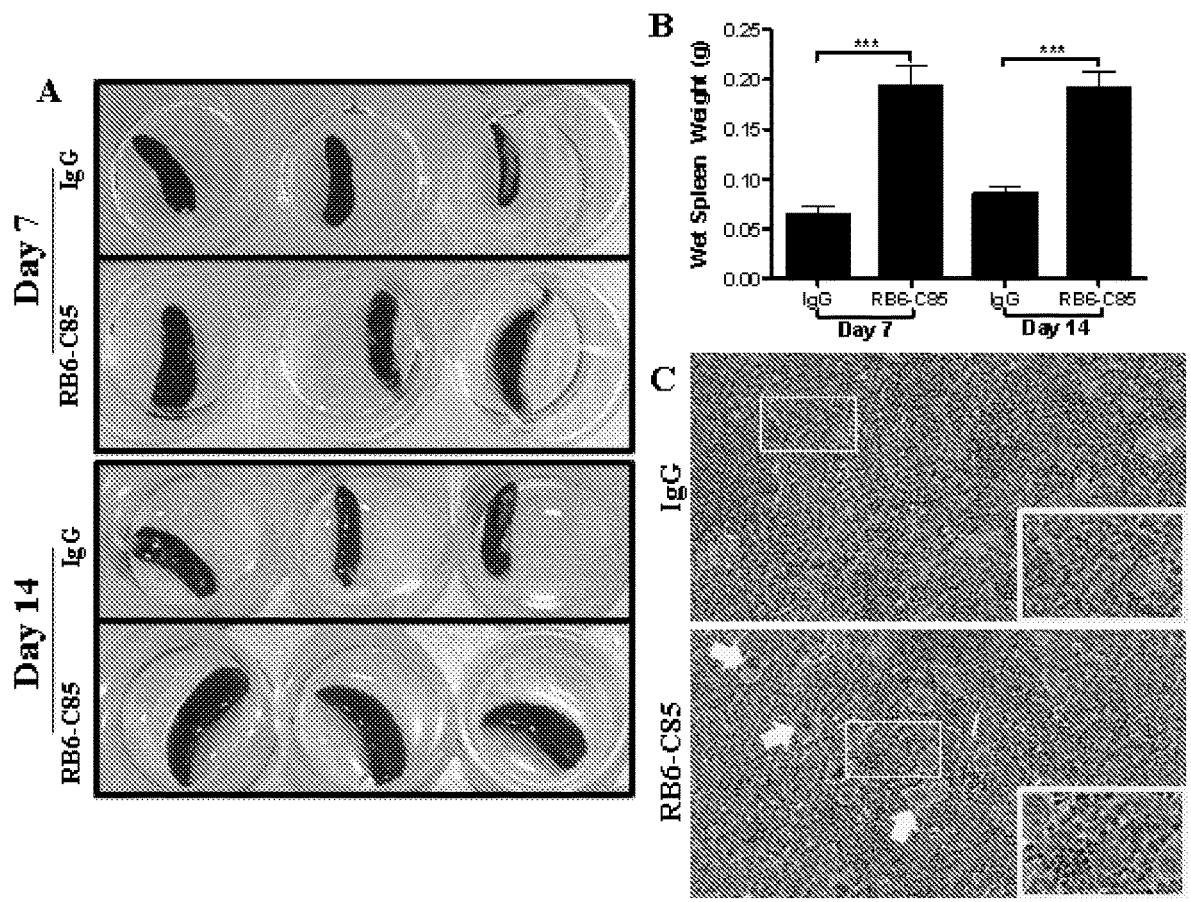
FIG. 13. RB6-C85 treatment leads to splenomegaly and extramedullary hematopoiesis during S. aureus orthopedic biofilm infection. Gross appearance (A) and weight (B) of spleens from RB6-C85- or IgG-treated mice at days 7 and 14 after S. aureus orthopedic biofilm infection (n=10 per group). (C) H&E-stained sections of spleens from IgG- and RB6-C85-treated mice at day 14 post-infection (n=3/group; 40× magnification; zoomed images (60×) depict areas delineated by rectangles in the 40× field of view). Arrows indicate presence of megakaryocytes in RB6-C85-treated spleens. Significant differences between IgG and RB6-C85 animals are denoted by asterisks (***, $p<0.001$; unpaired two-tailed Student t-test).

Targeting Gr-1$^+$ cells by RB6-C85 administration not only increased bacterial burdens and inflammation at the site of S. aureus orthopedic biofilm infection, it also led to significant systemic effects. First, Gr-1$^+$ depletion enhanced S. aureus dissemination, as bacterial burdens in the heart, kidney, and spleen of RB6-C85-treated animals were significantly elevated at day 7 post-infection compared to the isotype control group (FIG. 11C). Second, RB6-C85-treated animals displayed significant splenomegaly (FIGS. 13A and B). Histopathology revealed marked expansion of the splenic sinuses and red pulp with extensive extramedullary hematopoiesis, typified by numerous erythroid islands, megakaryoctyes, and leukocyte islands in RB6-C85-treated animals, which was not observed in infected isotype control mice (FIG. 13C).

Figure 14:
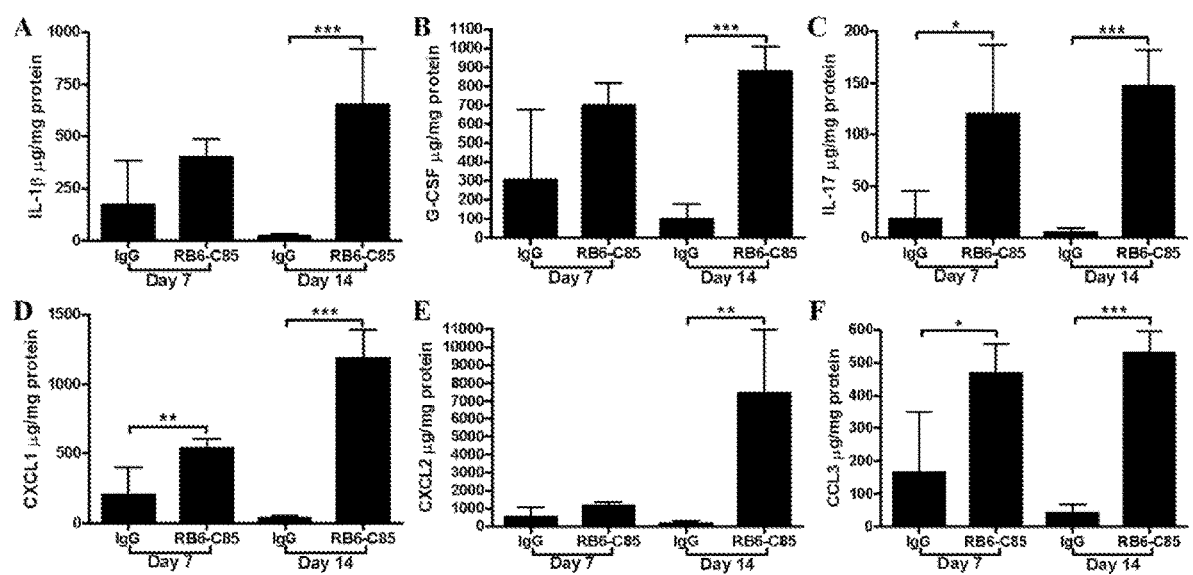
FIG. 14. RB6-C85 administration exacerbates inflammatory mediator production during S. aureus orthopedic biofilm infection. Tissue homogenates surrounding orthopedic implants were prepared at days 7 and 14 post-infection from RB6-C85- and isotype control-treated mice, whereupon IL-1β (A), G-CSF (B), IL-17 (C), CXCL1 (D), CXCL2 (E), and CCL3 (F) expression was quantitated by MILLIPLEX. Results were normalized to the amount of total protein recovered to correct for alterations in tissue sampling size. Significant differences are denoted by asterisks (*$p<0.05$; , $p<0.01$; *, $p<0.001$; unpaired two-tailed Student t-test) and are representative of five mice per group.

To examine changes in the inflammatory milieu after RB6-C85 treatment, inflammatory mediator expression was assessed. Numerous cytokines (IL-1β, G-CSF, and IL-17) and chemokines (CXCL1, CXCL2, and CCL3) were significantly increased at days 7 and 14 post-infection in RB6-C85-treated animals compared to isotype controls (FIG. 14). Similar changes were observed in the infected knee joint and femur. Taken together with the results from 1A8 depletion, these findings demonstrate that MDSCs are critical for limiting the proinflammatory activity of monocytes and macrophages during *S. aureus* biofilm infection, which sets the stage for bacterial persistence.

REFERENCES

1. Zhang, C., G. S. Lei, S. Shao, H. W. Jung, P. J. Durant, and C. H. Lee. 2012. Accumulation of myeloid-derived suppressor cells in the lungs during *Pneumocystis* pneumonia. *Infection and immunity* 80: 3634-3641.
2. Serafini, P., I. Borrello, and V. Bronte. 2006. Myeloid suppressor cells in cancer: recruitment, phenotype, properties, and mechanisms of immune suppression. *Seminars in cancer biology* 16: 53-65.
3. Sica, A., and V. Bronte. 2007. Altered macrophage differentiation and immune dysfunction in tumor development. *The Journal of clinical investigation* 117: 1155-1166.
4. Gabrilovich, D. I., and S. Nagaraj. 2009. Myeloid-derived suppressor cells as regulators of the immune system. *Nature reviews. Immunology* 9: 162-174.
5. Ochoa, A. C., A. H. Zea, C. Hernandez, and P. C. Rodriguez. 2007. Arginase, prostaglandins, and myeloid-derived suppressor cells in renal cell carcinoma. *Clinical cancer research: an official journal of the American Association for Cancer Research* 13: 721s-726s.
6. Sander, L. E., S. D. Sackett, U. Dierssen, N. Beraza, R. P. Linke, M. Muller, J. M. Blander, F. Tacke, and C. Trautwein. 2010. Hepatic acute-phase proteins control innate immune responses during infection by promoting myeloid-derived suppressor cell function. *The Journal of experimental medicine* 207: 1453-1464.
7. Delano, M. J., P. O. Scumpia, J. S. Weinstein, D. Coco, S. Nagaraj, K. M. Kelly-Scumpia, K. A. O'Malley, J. L. Wynn, S. Antonenko, S. Z. Al-Quran, R. Swan, C. S. Chung, M. A. Atkinson, R. Ramphal, D. I. Gabrilovich, W. H. Reeves, A. Ayala, J. Phillips, D. Laface, P. G. Heyworth, M. Clare-Salzler, and L. L. Moldawer. 2007. MyD88-dependent expansion of an immature GR-1(+) CD11b(+) population induces T cell suppression and Th2 polarization in sepsis. *The Journal of experimental medicine* 204: 1463-1474.
8. Poe, S. L., M. Arora, T. B. Oriss, M. Yarlagadda, K. Isse, A. Khare, D. E. Levy, J. S. Lee, R. K. Mallampalli, Y. R. Chan, A. Ray, and P. Ray. 2013. STAT1-regulated lung MDSC-like cells produce IL-10 and efferocytose apoptotic neutrophils with relevance in resolution of bacterial pneumonia. *Mucosal immunology* 6: 189-199.
9. Rieber, N., A. Brand, A. Hector, U. Graepler-Mainka, M. Ost, I. Schafer, I. Wecker, D. Neri, A. Wirth, L. Mays, S. Zundel, J. Fuchs, R. Handgretinger, M. Stern, M. Hogardt, G. Doring, J. Riethmuller, M. Kormann, and D. Hartl. 2013. Flagellin induces myeloid-derived suppressor cells: implications for *Pseudomonas aeruginosa* infection in cystic fibrosis lung disease. *Journal of immunology* 190: 1276-1284.
10. Obregon-Henao, A., M. Henao-Tamayo, I. M. Orme, and D. J. Ordway. 2013. Gr1(int)CD11b(+) Myeloid-Derived Suppressor Cells in *Mycobacterium tuberculosis* Infection. *PloS one* 8: e80669.
11. Wenzel, R. P. 2007. Health care-associated infections: major issues in the early years of the 21st century. *Clinical infectious diseases: an official publication of the Infectious Diseases Society of America* 45 Suppl 1: S85-88.
12. Watkins, R. R., M. Z. David, and R. A. Salata. 2012. Current concepts on the virulence mechanisms of meticillin-resistant *Staphylococcus aureus*. *Journal of medical microbiology* 61: 1179-1193.
13. Osmon, D. R., A. D. Hanssen, and R. Patel. 2005. Prosthetic joint infection: criteria for future definitions. *Clinical orthopaedics and related research:* 89-90.
14. Prabhakara, R., J. M. Harro, J. G. Leid, M. Harris, and M. E. Shirtliff. 2011. Murine immune response to a chronic *Staphylococcus aureus* biofilm infection. *Infection and immunity* 79: 1789-1796.
15. Donlan, R. M., and J. W. Costerton. 2002. Biofilms: survival mechanisms of clinically relevant microorganisms. *Clinical microbiology reviews* 15: 167-193.
16. Thurlow, L. R., M. L. Hanke, T. Fritz, A. Angle, A. Aldrich, S. H. Williams, I. L. Engebretsen, K. W. Bayles, A. R. Horswill, and T. Kielian. 2011. *Staphylococcus aureus* biofilms prevent macrophage phagocytosis and attenuate inflammation in vivo. *Journal of immunology* 186: 6585-6596.
17. Ribechini, E., V. Greifenberg, S. Sandwick, and M. B. Lutz. 2010. Subsets, expansion and activation of myeloid-derived suppressor cells. *Medical microbiology and immunology* 199: 273-281.
18. Condamine, T., and D. I. Gabrilovich. 2011. Molecular mechanisms regulating myeloid-derived suppressor cell differentiation and function. *Trends in immunology* 32: 19-25.
19. Cuenca, A. G., M. J. Delano, K. M. Kelly-Scumpia, C. Moreno, P. O. Scumpia, D. M. Laface, P. G. Heyworth, P. A. Efron, and L. L. Moldawer. 2011. A paradoxical role for myeloid-derived suppressor cells in sepsis and trauma. *Molecular medicine* 17: 281-292.
20. Bernthal, N. M., A. I. Stavrakis, F. Billi, J. S. Cho, T. J. Kremen, S. I. Simon, A. L. Cheung, G. A. Finerman, J. R. Lieberman, J. S. Adams, and L. S. Miller. 2010. A mouse model of post-arthroplasty *Staphylococcus aureus* joint infection to evaluate in vivo the efficacy of antimicrobial implant coatings. *PloS one* 5: e12580.
21. Hanke, M. L., A. Angle, and T. Kielian. 2012. MyD88-dependent signaling influences fibrosis and alternative macrophage activation during *Staphylococcus aureus* biofilm infection. *PloS one* 7: e42476.
22. Herzenberg, L. A., J. Tung, W. A. Moore, L. A. Herzenberg, and D. R. Parks. 2006. Interpreting flow cytometry data: a guide for the perplexed. *Nature immunology* 7: 681-685.
23. Hanke, M. L., C. E. Heim, A. Angle, S. D. Sanderson, and T. Kielian. 2013. Targeting macrophage activation for the prevention and treatment of *Staphylococcus aureus* biofilm infections. *Journal of immunology* 190: 2159-2168.
24. Hanke, M. L., and T. Kielian. 2012. Deciphering mechanisms of staphylococcal biofilm evasion of host immunity. *Frontiers in cellular and infection microbiology* 2: 62.
25. Brudecki, L., D. A. Ferguson, C. E. McCall, and M. El Gazzar. 2012. Myeloid-derived suppressor cells evolve during sepsis and can enhance or attenuate the systemic inflammatory response. *Infection and immunity* 80: 2026-2034.
26. Ostrand-Rosenberg, S., and P. Sinha. 2009. Myeloid-derived suppressor cells: linking inflammation and cancer. *Journal of immunology* 182: 4499-4506.
27. Haverkamp, J. M., S. A. Crist, B. D. Elzey, C. Cimen, and T. L. Ratliff. 2011. In vivo suppressive function of myeloid-derived suppressor cells is limited to the inflammatory site. *European journal of immunology* 41: 749-759.
28. Ioannou, M., T. Alissafi, I. Lazaridis, G. Deraos, J. Matsoukas, A. Gravanis, V. Mastorodemos, A. Plaitakis, A. Sharpe, D. Boumpas, and P. Verginis. 2012. Crucial role of granulocytic myeloid-derived suppressor cells in the regulation of central nervous system autoimmune disease. *Journal of immunology* 188: 1136-1146.
29. Peranzoni, E., S. Zilio, I. Marigo, L. Dolcetti, P. Zanovello, S. Mandruzzato, and V. Bronte. 2010. Myeloid-derived suppressor cell heterogeneity and subset definition. *Current opinion in immunology* 22: 238-244.
30. Gabrilovich, D. I., V. Bronte, S. H. Chen, M. P. Colombo, A. Ochoa, S. Ostrand-Rosenberg, and H. Schreiber. 2007. The terminology issue for myeloid-derived suppressor cells. *Cancer research* 67: 425; author reply 426.
31. Maenhout, S. K., S. Van Lint, P. U. Emeagi, K. Thielemans, and J. L. Aerts. 2013. Enhanced suppressive capacity of tumor-infiltrating myeloid-derived suppressor cells compared to their peripheral counterparts. *International journal of cancer. Journal international du cancer.*
32. Lee, P. Y., J. X. Wang, E. Parisini, C. C. Dascher, and P. A. Nigrovic. 2013. Ly6 family proteins in neutrophil biology. *Journal of leukocyte biology.*
33. Prabhakara, R., J. M. Harro, J. G. Leid, A. D. Keegan, M. L. Prior, and M. E. Shirtliff. 2011. Suppression of the inflammatory immune response prevents the development of chronic biofilm infection due to methicillin-resistant *Staphylococcus aureus*. *Infection and immunity* 79: 5010-5018.
34. Niska, J. A., J. A. Meganck, J. R. Pribaz, J. H. Shahbazian, E. Lim, N. Zhang, B. W. Rice, A. Akin, R. I. Ramos, N. M. Bernthal, K. P. Francis, and L. S. Miller. 2012. Monitoring bacterial burden, inflammation and bone damage longitudinally using optical and muCT imaging in an orthopaedic implant infection in mice. *PloS one* 7: e47397.
35. Archer, N. K., J. M. Harro, and M. E. Shirtliff. 2013. Clearance of *Staphylococcus aureus* nasal carriage is T cell dependent and mediated through interleukin-17A expression and neutrophil influx. *Infection and immunity* 81: 2070-2075.
36. Pillay, J., T. Tak, V. M. Kamp, and L. Koenderman. 2013. Immune suppression by neutrophils and granulocytic myeloid-derived suppressor cells: similarities and differences. *Cellular and molecular life sciences: CMLS* 70: 3813-3827.
37. Saiwai, H., H. Kumamaru, Y. Ohkawa, K. Kubota, K. Kobayakawa, H. Yamada, T. Yokomizo, Y. Iwamoto, and S. Okada. 2013. Ly6C+Ly6G-Myeloid-derived suppressor cells play a critical role in the resolution of acute inflammation and the subsequent tissue repair process after spinal cord injury. *Journal of neurochemistry* 125: 74-88.
38. Rodriguez, P. C., C. P. Hernandez, D. Quiceno, S. M. Dubinett, J. Zabaleta, J. B. Ochoa, J. Gilbert, and A. C. Ochoa. 2005. Arginase I in myeloid suppressor cells is induced by COX-2 in lung carcinoma. *The Journal of experimental medicine* 202: 931-939.
39. Xiang, X., A. Poliakov, C. Liu, Y. Liu, Z. B. Deng, J. Wang, Z. Cheng, S. V. Shah, G. J. Wang, L. Zhang, W. E. Grizzle, J. Mobley, and H. G. Zhang. 2009. Induction of myeloid-derived suppressor cells by tumor exosomes. *International journal of cancer. Journal international du cancer* 124: 2621-2633.
40. Eruslanov, E., I. Daurkin, J. Ortiz, J. Vieweg, and S. Kusmartsev. 2010. Pivotal Advance: Tumor-mediated induction of myeloid-derived suppressor cells and M2-polarized macrophages by altering intracellular PGE (2) catabolism in myeloid cells. *Journal of leukocyte biology* 88: 839-848.
41. Wojtasiak, M., D. L. Pickett, M. D. Tate, S. L. Londrigan, S. Bedoui, A. G. Brooks, and P. C. Reading. 2010. Depletion of Gr-1+, but not Ly6G+, immune cells exacerbates virus replication and disease in an intranasal model of herpes simplex virus type 1 infection. *The Journal of general virology* 91: 2158-2166.
42. Carr, K. D., A. N. Sieve, M. Indramohan, T. J. Break, S. Lee, and R. E. Berg. 2011. Specific depletion reveals a novel role for neutrophil-mediated protection in the liver during *Listeria monocytogenes* infection. *European journal of immunology* 41: 2666-2676.
43. Ribes, S., T. Regen, T. Meister, S. C. Tauber, S. Schutze, A. Mildner, M. Mack, U. K. Hanisch, and R. Nau. 2013. Resistance of the brain to *Escherichia coli* K1 infection depends on MyD88 signaling and the contribution of neutrophils and monocytes. *Infection and immunity* 81: 1810-1819.
44. Serbina, N. V., and E. G. Pamer. 2006. Monocyte emigration from bone marrow during bacterial infection requires signals mediated by chemokine receptor CCR2. *Nature immunology* 7: 311-317.
45. Gordon, S., and P. R. Taylor. 2005. Monocyte and macrophage heterogeneity. *Nature reviews. Immunology* 5: 953-964.
46. Austyn, J. M., and S. Gordon. 1981. F4/80, a monoclonal antibody directed specifically against the mouse macrophage. *European journal of immunology* 11: 805-815.
47. Chandra, D., A. Jahangir, W. Quispe-Tintaya, M. H. Einstein, and C. Gravekamp. 2013. Myeloid-derived suppressor cells have a central role in attenuated *Listeria monocytogenes*-based immunotherapy against metastatic breast cancer in young and old mice. *British journal of cancer* 108: 2281-2290.
48. Zhu, X., J. P. Pribis, P. C. Rodriguez, S. M. Morris, Jr., Y. Vodovotz, T. R. Billiar, and J. B. Ochoa. 2013. The Central Role of Arginine Catabolism in T-Cell Dysfunction and Increased Susceptibility to Infection After Physical Injury. *Annals of surgery.*
49. Rodriguez, P. C., D. G. Quiceno, and A. C. Ochoa. 2007. L-arginine availability regulates T-lymphocyte cell-cycle progression. *Blood* 109: 1568-1573.
50. Rodriguez, P. C., A. H. Zea, J. DeSalvo, K. S. Culotta, J. Zabaleta, D. G. Quiceno, J. B. Ochoa, and A. C. Ochoa. 2003. L-arginine consumption by macrophages modulates the expression of CD3 zeta chain in T lymphocytes. *Journal of immunology* 171: 1232-1239.
51. Makarenkova, V. P., V. Bansal, B. M. Matta, L. A. Perez, and J. B. Ochoa. 2006. CD11b+/Gr-1+ myeloid suppressor cells cause T cell dysfunction after traumatic stress. *Journal of immunology* 176: 2085-2094.
52. Josefowicz, S. Z., L. F. Lu, and A. Y. Rudensky. 2012. Regulatory T cells: mechanisms of differentiation and function. *Annual review of immunology* 30: 531-564.

53. Voyich, J. M., K. R. Braughton, D. E. Sturdevant, A. R. Whitney, B. Said-Salim, S. F. Porcella, R. D. Long, D. W. Dorward, D. J. Gardner, B. N. Kreiswirth, J. M. Musser, and F. R. DeLeo. 2005. Insights into mechanisms used by *Staphylococcus aureus* to avoid destruction by human neutrophils. *Journal of immunology* 175: 3907-3919.

54. Palazzolo-Ballance, A. M., M. L. Reniere, K. R. Braughton, D. E. Sturdevant, M. Otto, B. N. Kreiswirth, E. P. Skaar, and F. R. DeLeo. 2008. Neutrophil microbicides induce a pathogen survival response in community-associated methicillin-resistant *Staphylococcus aureus*. *Journal of immunology* 180: 500-509.

55. Cho, J. S., Y. Guo, R. I. Ramos, F. Hebroni, S. B. Plaisier, C. Xuan, J. L. Granick, H. Matsushima, A. Takashima, Y. Iwakura, A. L. Cheung, G. Cheng, D. J. Lee, S. I. Simon, and L. S. Miller. 2012. Neutrophil-derived IL-1beta is sufficient for abscess formation in immunity against *Staphylococcus aureus* in mice. *PLoS pathogens* 8: e1003047.

56. Rigby, K. M., and F. R. DeLeo. 2012. Neutrophils in innate host defense against *Staphylococcus aureus* infections. *Seminars in immunopathology* 34: 237-259.

57. Gabrilovich, D. I., M. P. Velders, E. M. Sotomayor, and W. M. Kast. 2001. Mechanism of immune dysfunction in cancer mediated by immature Gr-1+ myeloid cells. *Journal of immunology* 166: 5398-5406.

58. Kusmartsev, S., and D. I. Gabrilovich. 2003. Inhibition of myeloid cell differentiation in cancer: the role of reactive oxygen species. *Journal of leukocyte biology* 74: 186-196.

59. Ollivere, B., J. A. Wimhurst, I. M. Clark, and S. T. Donell. 2012. Current concepts in osteolysis. *The Journal of bone and joint surgery. British volume* 94: 10-15.

60. Abu-Amer, Y. 2009. Inflammation, cancer, and bone loss. *Current opinion in pharmacology* 9: 427-433.

61. Purdue, P. E., P. Koulouvaris, H. G. Potter, B. J. Nestor, and T. P. Sculco. 2007. The cellular and molecular biology of periprosthetic osteolysis. *Clinical orthopaedics and related research* 454: 251-261.

62. Burton, L., D. Paget, N. B. Binder, K. Bohnert, B. J. Nestor, T. P. Sculco, L. Santambrogio, F. P. Ross, S. R. Goldring, and P. E. Purdue. 2013. Orthopedic wear debris mediated inflammatory osteolysis is mediated in part by NALP3 inflammasome activation. *Journal of orthopaedic research: official publication of the Orthopaedic Research Society* 31: 73-80.

63. Epstein, N. J., B. A. Warme, J. Spanogle, T. Ma, B. Bragg, R. L. Smith, and S. B. Goodman. 2005. Interleukin-1 modulates periprosthetic tissue formation in an intramedullary model of particle-induced inflammation. *Journal of orthopaedic research: official publication of the Orthopaedic Research Society* 23: 501-510.

64. Shi, S., and X. Zhang. 2012. Interaction of *Staphylococcus aureus* with osteoblasts (Review). *Experimental and therapeutic medicine* 3: 367-370.

65. Cassat, J. E., N. D. Hammer, J. P. Campbell, M. A. Benson, D. S. Perrien, L. N. Mrak, M. S. Smeltzer, V. J. Tones, and E. P. Skaar. 2013. A secreted bacterial protease tailors the *Staphylococcus aureus* virulence repertoire to modulate bone remodeling during osteomyelitis. *Cell host & microbe* 13: 759-772.

66. Kristian, S. A., T. A. Birkenstock, U. Sauder, D. Mack, F. Gotz, and R. Landmann. 2008. Biofilm formation induces C3a release and protects *Staphylococcus epidermidis* from IgG and complement deposition and from neutrophil-dependent killing. *The Journal of infectious diseases* 197: 1028-1035.

67. Cerca, F., F. Andrade, A. Franca, E. B. Andrade, A. Ribeiro, A. A. Almeida, N. Cerca, G. Pier, J. Azeredo, and M. Vilanova. 2011. *Staphylococcus epidermidis* biofilms with higher proportions of dormant bacteria induce a lower activation of murine macrophages. *Journal of medical microbiology* 60: 1717-1724.

68. Schommer, N. N., M. Christner, M. Hentschke, K. Ruckdeschel, M. Aepfelbacher, and H. Rohde. 2011. *Staphylococcus epidermidis* uses distinct mechanisms of biofilm formation to interfere with phagocytosis and activation of mouse macrophage-like cells 774A.1. *Infection and immunity* 79: 2267-2276.

69. Spiliopoulou, A. I., F. Kolonitsiou, M. I. Krevvata, M. Leontsinidis, T. S. Wilkinson, D. Mack, and E. D. Anastassiou. 2012. Bacterial adhesion, intracellular survival and cytokine induction upon stimulation of mononuclear cells with planktonic or biofilm phase *Staphylococcus epidermidis*. *FEMS microbiology letters* 330: 56-65.

70. Scherr, T. D., C. M. Roux, M. L. Hanke, A. Angle, P. M. Dunman, and T. Kielian. 2013. Global transcriptome analysis of *Staphylococcus aureus* biofilms in response to innate immune cells. *Infection and immunity* 81: 4363-4376.

71. Gunther, F., G. H. Wabnitz, P. Stroh, B. Prior, U. Obst, Y. Samstag, C. Wagner, and G. M. Hansch. 2009. Host defence against *Staphylococcus aureus* biofilms infection: phagocytosis of biofilms by polymorphonuclear neutrophils (PMN). *Molecular immunology* 46: 1805-1813.

72. Graves, S. F., S. D. Kobayashi, and F. R. DeLeo. 2010. Community-associated methicillin-resistant *Staphylococcus aureus* immune evasion and virulence. *Journal of molecular medicine* 88: 109-114.

Each reference cited herein is hereby incorporated by reference in its entirety, or in pertinent part, as will become evident from the context of the citation. From the foregoing it will be appreciated that, although specific embodiments of the disclosure have been described herein for purposes of illustration, various modifications may be made without deviating from the spirit and scope of the disclosure.

What is claimed is:

1. A method of treating a biofilm infection comprising administering a therapeutically effective amount of an isolated inhibitor of a myeloid-derived suppressor cell selected from the group consisting of a Signal Transducer and Activator of Transcription 3- (STAT3)-targeted small interfering RNA (siRNA), a Janus kinase (JAK) inhibitor, an anti-CD15 (stage-specific embryonic antigen (SSEA-1)), an anti-CD33, an anti-CD34, an anti-CD66b, an anti-CD162, an anti-MRP-14 (anti-S100 calcium binding protein A9 (anti-S100A9)), an anti-nuclear factor kappa B p50 subunit (anti-NF-kB (p50)) antibody, an anti-Src homology 2 domain containing inositol polyphosphate 5-phosphatase 1 (anti-SHIP-1) antibody, an anti-STAT1 antibody, an indoleamine 2,3-dioxygenase (IDO) inhibitor other than rosmarinic acid, a nuclear factor erythroid 2-related factor 2 (Nrf-2) activator, an interleukin 10 (IL-10) inhibitor, an IL-10 receptor inhibitor, an arginase inhibitor, stattic, galiellalactone, GLG-101, GLG-202, GLG-302, GLG-401 and OPB-31121.

2. The method of claim 1 wherein the myeloid-derived suppressor cell (MDSC) is a $CD11b^+$ $Ly\text{-}6G/Ly\text{-}6C^+$ $(Gr\text{-}1^+)$ MDSC.

3. The method of claim 1 wherein the arginase inhibitor is C-201 or C-301; or the IDO inhibitor is INCB24360, norharmane, 1-methyltryptophan, a tryptophan derivative, Indoximod, or NLG919; or the JAK inhibitor is AZD1480, tofacitinib, ruxolitinib, baricitinib, decernotinib, GPLGO34, CEP-701 (lestaurtinib), INCB39110, INCB16562, INCB47986, SB1518 (pacritinib), SAR302503, XL019, or NVP-BSK805; or the Nrf-2 activator is RTA-408.

4. The method of claim 1 wherein the biofilm is associated with an artificial substance in vivo.

5. The method of claim 1 wherein the biofilm infection is a *Staphylococcus* infection or a *Pseudomonas* infection.

6. The method of claim 5 wherein the *Staphylococcus* infection is a methicillin-resistant *Staphylococcus aureus* (MRSA) infection.

7. A method of treating a biofilm infection comprising administering a therapeutically effective amount of an isolated inhibitor of a myeloid-derived suppressor cell, wherein the isolated inhibitor of a myeloid-derived suppressor cell is GLG-302.

\* \* \* \* \*